(12) United States Patent
Chase et al.

(10) Patent No.: US 11,559,683 B2
(45) Date of Patent: Jan. 24, 2023

(54) METHOD AND DEVICE FOR TREATING SLEEP RELATED BREATHING DISORDERS

(71) Applicant: Zennea Technologies Inc., Surrey (CA)

(72) Inventors: Rachel Chase, Surrey (CA); Jia Du, Surrey (CA); Oliver Luo, Richmond (CA); Ryan Threlfall, Quesnel (CA)

(73) Assignee: Zennea Technologies Inc., Vancouver (CA)

( * ) Notice: Subject to any disclaimer, the term of this patent is extended or adjusted under 35 U.S.C. 154(b) by 149 days.

(21) Appl. No.: 17/056,842

(22) PCT Filed: May 27, 2019

(86) PCT No.: PCT/CA2019/050720
§ 371 (c)(1),
(2) Date: Nov. 19, 2020

(87) PCT Pub. No.: WO2019/227203
PCT Pub. Date: Dec. 5, 2019

(65) Prior Publication Data
US 2021/0162211 A1 Jun. 3, 2021

Related U.S. Application Data

(60) Provisional application No. 62/679,496, filed on Jun. 1, 2018.

(51) Int. Cl.
*A61N 1/36* (2006.01)
*A61N 1/04* (2006.01)
*A61F 5/56* (2006.01)

(52) U.S. Cl.
CPC ......... *A61N 1/3601* (2013.01); *A61N 1/0456* (2013.01); *A61N 1/36031* (2017.08);
(Continued)

(58) Field of Classification Search
CPC ................ A61N 1/3601; A61N 1/0456; A61N 1/36031; A61N 1/36034
See application file for complete search history.

(56) References Cited

U.S. PATENT DOCUMENTS 4,996,987 A * 3/1991 Petrofsky ........... A61N 1/36003
607/66
5,123,425 A 6/1992 Shannon, Jr. et al.
(Continued)

FOREIGN PATENT DOCUMENTS

WO 2016/124739 A1 8/2016

*Primary Examiner* — Unsu Jung
*Assistant Examiner* — Philip C Edwards
(74) *Attorney, Agent, or Firm* — Larson & Anderson, LLC

(57) ABSTRACT

The present disclosure relates to a method for increasing an amount of air and/or oxygen passing through an airway of an individual, reducing airway restrictions in an individual, increasing airway patency and/or maintaining airway patency in an individual, decreasing snoring, obstructive sleep apnea, or a combination thereof, in an individual. The method may comprise stimulating at least four regions of the individual's neck, where two of the at least four regions of the individual's neck are anterior triangle regions on opposing sides of the individual's midline, and another two of the at least four regions of the individual's neck are anterior triangle regions on opposing sides of the individual's midline, posterior to the two of the at least four regions. The present disclosure also discusses related devices and systems.

19 Claims, 11 Drawing Sheets

(52) U.S. Cl.
CPC ............ *A61N 1/36034* (2017.08); *A61F 5/56* (2013.01); *A61N 1/0496* (2013.01)

(56) References Cited

U.S. PATENT DOCUMENTS

| | | | |
|---|---|---|---|
| 5,178,156 | A | 1/1993 | Takishima et al. |
| 5,265,624 | A | 11/1993 | Bowman |
| 5,281,219 | A | 1/1994 | Kallok |
| 5,591,216 | A | 1/1997 | Testerman et al. |
| 5,877,472 | A | 3/1999 | Campbell |
| 6,251,126 | B1 | 6/2001 | Ottenhoff et al. |
| 6,587,725 | B1 | 7/2003 | Durand et al. |
| 7,473,227 | B2 | 1/2009 | Hsu et al. |
| 7,644,714 | B2 | 1/2010 | Atkinson et al. |
| 7,680,538 | B2 | 3/2010 | Durand et al. |
| 7,742,828 | B2 | 6/2010 | Gadsby et al. |
| 7,809,442 | B2 | 10/2010 | Bolea et al. |
| 8,249,723 | B2 | 8/2012 | McCreery |
| 8,473,058 | B2 | 6/2013 | Sasaki et al. |
| 9,114,256 | B2 | 8/2015 | El Achhab et al. |
| 9,186,504 | B2 | 11/2015 | Gross |
| 9,308,370 | B2 | 4/2016 | Lima et al. |
| 9,415,216 | B2 | 8/2016 | Mashiach |
| 9,457,186 | B2 | 10/2016 | Gross |
| 9,463,318 | B2 | 10/2016 | Mashiach et al. |
| 9,649,493 | B2 | 5/2017 | Mashiach |
| 9,656,083 | B2 | 5/2017 | Meadows et al. |
| 9,757,560 | B2 | 9/2017 | Papay |
| 9,821,165 | B2 | 11/2017 | Gross |
| 9,833,613 | B2 | 12/2017 | Sama |
| 9,849,289 | B2 | 12/2017 | Mashiach et al. |
| 9,855,032 | B2 | 1/2018 | Mashiach et al. |
| 9,907,967 | B2 | 3/2018 | Mashiach et al. |
| 9,943,686 | B2 | 4/2018 | Mashiach |
| 9,993,652 | B2 | 6/2018 | Mashiach et al. |
| 10,058,701 | B2 | 8/2018 | Sama |
| 10,561,836 | B2 | 2/2020 | Sama |
| 10,596,366 | B2 | 3/2020 | Sama |
| 2003/0199945 | A1 | 10/2003 | Ciulla |
| 2004/0111139 | A1 | 6/2004 | McCreery |
| 2005/0085874 | A1 | 4/2005 | Davis et al. |
| 2008/0021506 | A1 | 1/2008 | Grocela |
| 2008/0082153 | A1 | 4/2008 | Gadsby et al. |
| 2011/0093032 | A1 | 4/2011 | Bogg, II et al. |
| 2011/0230702 | A1 | 9/2011 | Honour |
| 2012/0123498 | A1 | 5/2012 | Gross |
| 2013/0226275 | A1* | 8/2013 | Duncan ............... A61N 1/36021 607/152 |
| 2013/0261693 | A1 | 10/2013 | Gross |
| 2014/0083434 | A1 | 3/2014 | Groteke |
| 2014/0135868 | A1* | 5/2014 | Bashyam ............. A61N 1/3601 607/42 |
| 2014/0307040 | A1 | 10/2014 | Choi et al. |
| 2014/0379049 | A1 | 12/2014 | Mashiach et al. |
| 2015/0018895 | A1* | 1/2015 | El Achhab ......... A61N 1/36034 607/42 |
| 2015/0032177 | A1 | 1/2015 | Mashiach et al. |
| 2015/0039046 | A1 | 2/2015 | Gross |
| 2015/0142120 | A1 | 5/2015 | Papay |
| 2015/0148861 | A1 | 5/2015 | Gross |
| 2015/0224018 | A1 | 8/2015 | Graindorge et al. |
| 2016/0030740 | A1 | 2/2016 | Mashiach |
| 2016/0317803 | A1 | 11/2016 | Sama |
| 2017/0007829 | A1 | 1/2017 | Gross |
| 2017/0165101 | A1 | 6/2017 | Davidian |
| 2017/0246463 | A1 | 8/2017 | Mashiach et al. |
| 2017/0304612 | A1 | 10/2017 | Sama |
| 2018/0015281 | A1 | 1/2018 | Strohl |
| 2018/0229028 | A1 | 8/2018 | Sama |
| 2019/0099598 | A1 | 4/2019 | Sama |
| 2020/0121921 | A1 | 4/2020 | Sama |
| 2020/0121924 | A1 | 4/2020 | Sama |
| 2020/0121984 | A1 | 4/2020 | Sama |
| 2020/0164205 | A1 | 5/2020 | Sama |

\* cited by examiner

METHOD AND DEVICE FOR TREATING SLEEP RELATED BREATHING DISORDERS

FIELD

The present disclosure relates to a device for treating sleep related breathing disorders, and methods and systems related thereto.

BACKGROUND

Snoring is a common chronic ailment that affects a large global population. Snoring is commonly caused by muscles in the tongue and/or associated upper airway muscles to relax, which causes the muscles to partially block the airway and vibrate as the body pushes air through the restricted airway. Snoring can disrupt an individual's, and their partner's, deep sleep and can cause sleep deprivation, which has negative long-term health effects.

Obstructive sleep apnea affects a large segment of the population; a segment that will continue to grow with the global populations' increasing obesity rates. Obstructive sleep apnea is caused by muscles relaxing around the airway and blocking the airway. Obstructive sleep apnea reduces the amount of time an individual stays in restorative phase of sleep including rapid eye movement (REM), and therefore, may cause daytime fatigue.

Restricting airflow in an individual's airway may cause hypoxemia and pose significant long-term negative side effects including hypertension, heart problems, an increased risk of stroke, heart disease, and diabetes, and cognitive deficiency.

One known method for treating snoring and/or sleep apnea is the use of a continuous positive airway pressure (CPAP) device. A CPAP device continuously forces pressurized air through a restricted or blocked air passage via a mask that covers the face and/or nose of an individual, and is connected by a hose to a machine to pump pressurized air to keep the individual's airway open while sleeping. Other known treatment devices include Mandibular Advancement Devices, Provent Therapy, chin straps, and surgery.

Improvements in treating sleep related breathing disorders, for example, snoring and sleep apnea, are desirable.

SUMMARY

One or more previously proposed methods and devices used to treat snoring and/or obstructive sleep apnea may: (1) imprecisely target the muscles required to open an individual's airway, which may, for example, cause uneven activation of muscles leading to further airway blockages; (2) imprecisely provide stimulation to an individual's muscles, which may, for example, cause muscle fatigue, cause facial nerve twitches, cause choking hazards, increase the risk of voltage surges, and/or affect an individual's ability to enter slow wave and/or REM sleep; (3) be overly invasive, such as surgery; (4) alter the natural alignment of the jaw; (5) cause skin irritations and/or skin rashes; or (6) a combination thereof.

The present disclosure describes a method that activates each of an individual's pair of hypoglossal nerves at at least two regions to cause contraction of at least one of the individual's muscles that controls the motion of the individual's tongue and innervated by the hypoglossal nerve, for example, the genioglossus muscle, the hyoglossus muscle, the digastric anterior muscle, the mylohyoid muscle, the geniohyoid muscle, the styoglossus muscle, the superior longitudinal muscle, the inferior longitudinal muscle, the transverse muscle, the vertical muscle, or a combination thereof, to: decrease the incidence of the individual's tongue from falling into the oropharyngeal space and restricting the individual's airway space, decrease the incidence of the individual's epiglottis from falling into the laryngopharynx space, or a combination thereof. Optionally, avoiding activating facial nerves. The present disclosure also describes devices and systems for implementing the above-described method.

One or more examples of the methods, devices, and systems according to the present disclosure may: (1) increase the effectiveness and/or increase the efficiency of increasing the amount of air and/or oxygen passing through a individual's airway; (2) reduce airway restrictions in an individual; (3) increase airway patency in an individual and/or maintain an individual's airway patency; (4) decrease snoring, obstructive sleep apnea, or a combination thereof; (5) reduce the amount of electrical current delivered to an individual's body; (6) increase the safety/decrease harm during use; (7) reduce muscle fatigue; (8) decrease disruption of a individual's sleep; (9) decrease disruption of slow wave sleep and/or rapid eye movement (REM) when using the device; or (10) a combination thereof, in comparison to methods, devices, and systems that do not activate each of an individual's pair of hypoglossal nerves at at least two regions according to the present disclosure.

The present disclosure provides a method for increasing an amount of air and/or oxygen passing through an airway of an individual, the method comprising the step of: stimulating at least four regions of the individual's neck, wherein two of the at least four regions of the individual's neck are anterior triangle regions on opposing sides of the individual's midline, and another two of the at least four regions of the individual's neck are anterior triangle regions on opposing sides of the individual's midline, posterior to the two of the at least four regions. The individual may be sleeping.

The present disclosure also provides a method for reducing airway restrictions in an individual, the method comprising the step of: stimulating at least four regions of the individual's neck, wherein two of the at least four regions of the individual's neck are anterior triangle regions on opposing sides of the individual's midline, and another two of the at least four regions of the individual's neck are anterior triangle regions on opposing sides of the individual's midline, posterior to the two of the at least four regions. The individual may be sleeping.

The present disclosure also provides a method for increasing airway patency and/or maintaining airway patency in an individual, the method comprising the step of: stimulating at least four regions of the individual's neck, wherein two of the at least four regions of the individual's neck are anterior triangle regions on opposing sides of the individual's midline, and another two of the at least four regions of the individual's neck are anterior triangle regions on opposing sides of the individual's midline, posterior to the two of the at least four regions. The individual may be sleeping.

The present disclosure also provides a method for decreasing snoring, obstructive sleep apnea, or a combination thereof in an individual, the method comprising the step of: stimulating at least four regions of the individual's neck, wherein two of the at least four regions of the individual's neck are anterior triangle regions on opposing sides of the individual's midline, and another two of the at least four regions of the individual's neck are anterior triangle regions on opposing sides of the individual's midline, posterior to the two of the at least four regions.

The two of the at least four regions may be submental triangle regions on opposing sides of the individual's midline, and the another two of the at least four regions may be submandibular regions on opposing sides of the individual's midline. The two of the at least four regions may be a pair of first regions of the individual's hypoglossal nerves and the another two of the at least four regions may be a pair of second regions of the individual's pair of hypoglossal nerves, the pair of second regions being anterior to the pair of first regions. The pair of first regions of the hypoglossal nerves may be a pair of regions anterior of the point where the hypoglossal nerves split between a medial contingent and a lateral contingent. The pair of first regions of the hypoglossal nerves may be the medial contingent. The pair of second regions of the hypoglossal nerves may be a pair of regions posterior of the point where the hypoglossal nerves split between a medial contingent and a lateral contingent.

Stimulating may comprise passing a current between the two of the at least four regions of the individual's neck and the another two of the at least four regions of the individual's neck, on the same side of the individual's midline. Passing a current between the two of the at least four regions of the individual's neck and the another two of the at least four regions of the individual's neck, on the same side of the individual's midline may comprise passing a current from the two of the at least four regions of the individual's neck to the another two of the at least four regions of the individual's neck.

The current may be produced by at least two types of waveform modulations. At least a first type of the at least two types of waveform modulations may be a low-intensity, high frequency waveform and another type of the at least two types of waveform modulations may be a high-intensity, low-frequency waveform. The high-intensity, low-frequency waveform may comprise at least two pulses, wherein one of the at least two pulses is positive in magnitude and another pulse of the at least two pulses is negative in magnitude. The at least two pulses may have a frequency from about 1 Hz to about 20 Hz. The at least two pulses may have a pulse width from about 100 µs to about 400 µs. The low-intensity, high frequency waveform may comprise at least two pulses, wherein one of the at least two pulses is positive in magnitude and another pulse of the at least two pulses is negative in magnitude. The at least two pulses may have a frequency from about 20 Hz to about 100 Hz. The current has a duty cycle of up to about 1%. The amount of current may be from about 1 milliampere to about 33 milliamperes.

The stimulation may be transcutaneous stimulation.

The herein described method may further comprise positioning a device comprising at least four stimulators for stimulating the at least four regions of the individual's airway on the individual's neck. The at least four stimulators may be positioned on the individual's neck using a removable adhesive. The at least four stimulators may be oriented in fixed positions relative to one another to stimulate the at least four regions of the individual's neck.

The herein described method may further comprise the step of stimulating the at least four regions of the individual's neck with increasing increments of stimulation intensity until a threshold is met.

The herein described method may further comprise a step of increasing and/or decreasing increments of stimulation intensity once the threshold is met.

The present disclosure also provides a device for increasing the amount of oxygen passing through the airway of an individual, the device comprising: at least four stimulators for stimulating at least four regions of the individual's neck, wherein two of the at least four stimulators are for stimulating two of the at least four regions of the individual's neck that are anterior triangle regions on opposing sides of the individual's midline, and another two of the at least stimulators are for stimulating another two of the at least four regions of the individual's neck that are anterior triangle regions on opposing sides of the individual's midline, posterior to the two of the at least four regions; and at least one processor in electrical communication with the at least four stimulators to control the electrical stimulation.

The present disclosure also provides a device for reducing airway restrictions in an individual, the device comprising: at least four stimulators for stimulating at least four regions of the individual's neck, wherein two of the at least four stimulators are for stimulating two of the at least four regions of the individual's neck that are anterior triangle regions on opposing sides of the individual's midline, and another two of the at least stimulators are for stimulating another two of the at least four regions of the individual's neck that are anterior triangle regions on opposing sides of the individual's midline, posterior to the two of the at least four regions; and at least one processor in electrical communication with the at least four stimulators to control the electrical stimulation.

The present disclosure also provides a device for increasing airway patency and/or maintaining airway patency in an individual, the device comprising: at least four stimulators for stimulating at least four regions of the individual's neck, wherein two of the at least four stimulators are for stimulating two of the at least four regions of the individual's neck that are anterior triangle regions on opposing sides of the individual's midline, and another two of the at least stimulators are for stimulating another two of the at least four regions of the individual's neck that are anterior triangle regions on opposing sides of the individual's midline, posterior to the two of the at least four regions; and at least one processor in electrical communication with the at least four stimulators to control the electrical stimulation.

The present disclosure also provides a device for decreasing snoring, obstructive sleep apnea, or a combination thereof in an individual, the device comprising: at least four stimulators for stimulating at least four regions of the individual's neck, wherein two of the at least four stimulators are for stimulating two of the at least four regions of the individual's neck that are anterior triangle regions on opposing sides of the individual's midline, and another two of the at least stimulators are for stimulating another two of the at least four regions of the individual's neck that are anterior triangle regions on opposing sides of the individual's midline, posterior to the two of the at least four regions; and at least one processor in electrical communication with the at least four stimulators to control the electrical stimulation.

The at least four stimulators may be transcutaneous stimulators. The at least four stimulators may be gold-plated or silver-plated copper electrodes.

The at least four stimulators may be oriented in fixed positions relative to one another for stimulating the at least four regions of the individual's neck. The herein described device may be couplable to the individual's neck using at least one removable adhesive. The device may be couplable to hydrogel that is in electrical communication with at least a portion of the at least four stimulators. The orientation of the hydrogel when coupled to the device may be for conducting the electrical stimulation from the at least four stimulators to the at least four regions of the individual's neck and may be for preventing conducting of the electrical stimulation from the at least four stimulators to the individual's neck at regions other than the at least four regions. The hydrogel may be couplable to at least one removable adhesive.

The herein described device may have an L-shaped body comprising a first stem and a second stem, the first stem may comprise two of the at least four stimulators for stimulating two of the at least four regions of the individual's neck on one side of the individual's midline, the second stem may comprise another two of the at least four stimulators for stimulating another two of the at least four regions of the individual's neck on the second side of the individual's midline.

The at least four regions of the individual's neck stimulated in the herein described method may be stimulated by the herein described device.

The present disclosure also provides a system for increasing the amount of air passing through the airway of an individual, the system comprising: the herein described device; and a power source, coupled to the device for providing an electrical signal to the at least four stimulators.

The present disclosure also provides a system for reducing airway restrictions in an individual, the system comprising: the herein described device; and a power source, coupled to the device for providing an electrical signal to the at least four stimulators.

The present disclosure also provides a system for increasing airway patency and/or maintaining airway patency in an individual, the system comprising: the herein described device; and a power source, coupled to the device for providing an electrical signal to the at least four stimulators.

The present disclosure also provides a system for decreasing snoring, obstructive sleep apnea, or a combination thereof in an individual, the system comprising: the herein described device; and a power source, coupled to the device for providing an electrical signal to the at least four stimulators.

Other aspects and features of the present disclosure will become apparent to those ordinarily skilled in the art upon review of the following description of specific embodiments in conjunction with the accompanying figures.

BRIEF DESCRIPTION OF THE DRAWINGS

Embodiments of the present disclosure will now be described, by way of examples only, with reference to the attached Figures.

DETAILED DESCRIPTION

Figure 1A:
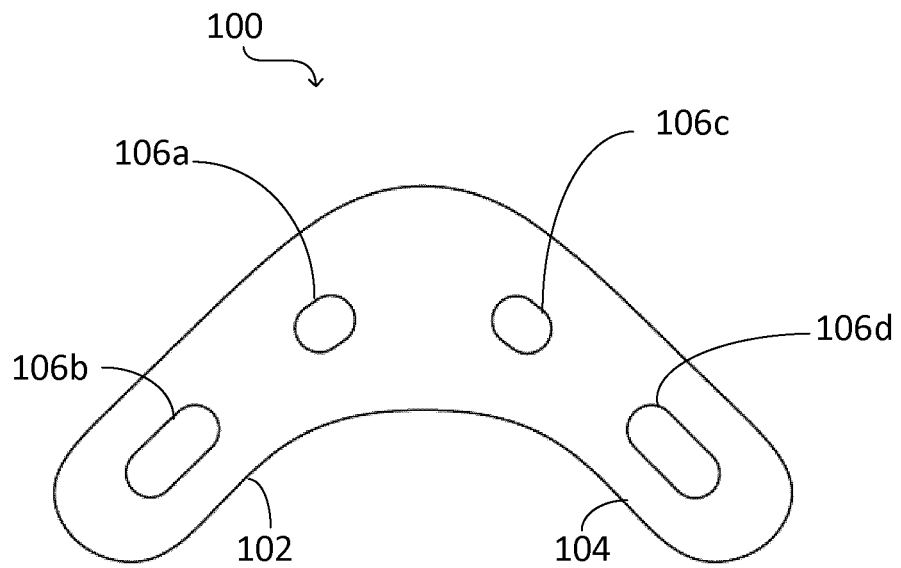
FIGS. 1A and B are illustrations of a device according to the present disclosure in top view (FIG. 1A) and bottom view (FIG. 1B).

Generally, the present disclosure provides a method for increasing the amount of air and/or oxygen passing through the airway of an individual. The method comprises the step of: stimulating at least four regions of the individual's neck, wherein two of the at least four regions of the individual's neck are anterior triangle regions on opposing sides of the individual's midline, and another two of the at least four regions of the individual's neck are anterior triangle regions on opposing sides of the individual's midline, posterior to the two of the at least four regions.

The present disclosure also provides a method for reducing airway restrictions in an individual. The method comprises the step of: stimulating at least four regions of the individual's neck, wherein two of the at least four regions of the individual's neck are anterior triangle regions on opposing sides of the individual's midline, and another two of the at least four regions of the individual's neck are anterior triangle regions on opposing sides of the individual's midline, posterior to the two of the at least four regions.

The present disclosure also provides a method for increasing airway patency and/or maintaining airway patency in an individual. The method comprises the step of: stimulating at least four regions of the individual's neck, wherein two of the at least four regions of the individual's neck are anterior triangle regions on opposing sides of the individual's midline, and another two of the at least four regions of the individual's neck are anterior triangle regions on opposing sides of the individual's midline, posterior to the two of the at least four regions.

The present disclosure also provides a method for decreasing snoring, decreasing obstructive sleep apnea, or a combination thereof in an individual. The method comprises the step of: stimulating at least four regions of the individual's neck, wherein two of the at least four regions of the individual's neck are anterior triangle regions on opposing sides of the individual's midline, and another two of the at least four regions of the individual's neck are anterior triangle regions on opposing sides of the individual's midline, posterior to the two of the at least four regions.

In the context of the present disclosure, an individual's airway refers to the path that air follows to move into and out of the individual's lungs. The mouth and nose of the individual are the normal entry and exit ports for the airway. Entering air passes through the pharynx and continues through the larynx, down the trachea, and through the bronchi. Optionally, the individual's airway refers to the pathway through the individual's pharynx and larynx.

Increasing the amount of air and/or oxygen refers to opening an individual's airway by controlling the contraction and relaxation states of at least one of the muscles that controls the motion of an individual's tongue and innervated by the hypoglossal nerve, for example, the genioglossus muscle, the hyoglossus muscle, the digastric anterior muscle, the mylohyoid muscle, the geniohyoid muscle, the styoglossus muscle, the superior longitudinal muscle, the inferior longitudinal muscle, the transverse muscle, the vertical muscle, or a combination thereof. Optionally, without activating the other pairs of extrinsic muscles of the tongue. Increasing the amount of air and/or oxygen to an individual may comprise increasing the amount of air and/or oxygen passing through the individual's airway by about 10%, about 20%, about 30%, about 40%, about 50%, about 60%, about 70%, about 75%, about 80%, about 85%, about 90%, about 95%, or 100% compared to the amount of air and/or oxygen passing though the individual's airway before stimulating at least four regions of the individual's neck according to the present disclosure. Optionally, increasing the amount of air and/or oxygen to an individual may comprise increasing the size of an individual's airway to about 10%, about 20%, about 30%, about 40%, about 50%, about 60%, about 70%, about 75%, about 80%, about 85%, about 90%, about 95%, or 100% of the normal size of the individual's airway opening before stimulating at least four regions of the individual's neck according to the present disclosure. Normal size refers to the size of the individual's airway opening when the individual is not suffering from snoring and/or obstructive sleep apnea.

Reducing airway restrictions refers to controlling the contraction and relaxation states of at least one of the muscles that controls the motion of an individual's tongue and innervated by the hypoglossal nerve, for example, the genioglossus muscle, the hyoglossus muscle, the digastric anterior muscle, the mylohyoid muscle, the geniohyoid muscle, the styoglossus muscle, the superior longitudinal muscle, the inferior longitudinal muscle, the transverse muscle, the vertical muscle, or a combination thereof, a sufficient amount to: 1) decrease and/or clear a blockage or obstruction in the individual's airway; 2) decrease the incidence of a blockage or obstruction forming in the individual's airway, or 3) a combination thereof. Optionally, without activating the other pairs of extrinsic muscles of the tongue. Decreasing and/or clearing an individual's airway blockage or obstruction may comprise decreasing the blockage or obstruction by about 10%; about 20%, by about 30%, by about 40%, by about 50%, by about 60%, by about 70%, by about 80%, by about 90%, or 100% compared to the individual's blockage or obstruction before stimulating at least four regions of the individual's neck according to the present disclosure. Optionally, decreasing and/or clearing an individual's airway blockage or obstruction may comprise increasing the airflow in the airway to about 10%, about 20%, about 30%, about 40%, about 50%, about 75%, about 80%, about 85%, about 90%, about 95%, or 100% of the airflow of the individual without the blockage or obstruction. Optionally, decreasing and/or clearing an individual's airway blockage or obstruction may comprise increasing the size of an individual's airway opening to about 10%, about 20%, about 30%, about 40%, about 50%, about 60%, about 70%, about 75%, about 80%, about 85%, about 90%, about 95%, or 100% of the normal size of the individual's airway opening before stimulating at least four regions of the individual's neck according to the present disclosure. Optionally, decreasing and/or clearing an individual's airway blockage or obstruction may comprise increasing the amount of air and/or oxygen passing through the individual's airway by about 10%, about 20%, about 30%, about 40%, about 50%, about 60%, about 70%, about 75%, about 80%, about 85%, about 90%, about 95%, or 100% compared to the amount of air and/or oxygen passing though the individual's airway before stimulating at least four regions of the individual's neck according to the present disclosure.

Decreasing the incidence of a blockage or obstruction forming in an individual's airway refers to decreasing the incidence of the individual's epiglottis from falling into the laryngopharynx space by about 5%, about 10%, about 20%, about 30%, about 40%, about 50%, about 60%, about 70%, about 75%, about 80%, about 85%, about 90%, about 95%, or 100% compared to the incidence of the individual's epiglottis falling into the laryngopharynx space before stimulating at least four regions of the individual's neck according to the present disclosure.

Increasing airway patency refers to opening an individual's airway by controlling the contraction and relaxation states of at least one of the muscles that controls the motion of an individual's tongue and innervated by the hypoglossal nerve, for example, the genioglossus muscle, the hyoglossus muscle, the digastric anterior muscle, the mylohyoid muscle, the geniohyoid muscle, the styoglossus muscle, the superior longitudinal muscle, the inferior longitudinal muscle, the transverse muscle, the vertical muscle, or a combination thereof, a sufficient amount to allow the individual to inhale oxygen and exhale carbon dioxide. Preferably, increasing airway patency to the individual's normal level. Normal level refers to the individual's patency when the individual is not suffering from snoring and/or obstructive sleep apnea. Optionally, without activating the other pairs of extrinsic muscles of the tongue. Increasing airway patency may comprise decreasing the blockage or obstruction by about 10%; about 20%, by about 30%, by about 40%, by about 50%, by about 60%, by about 70%, by about 80%, by about 90%, or 100% compared to the individual's blockage or obstruction before stimulating at least four regions of the individual's neck according to the present disclosure. Optionally, increasing airway patency may comprise increasing the size of an individual's airway opening to about 10%, about 20%, about 30%, about 40%, about 50%, about 60%, about 70%, about 75%, about 80%, about 85%, about 90%, about 95%, or 100% of the normal size of the individual's airway opening before stimulating at least four regions of the individual's neck according to the present disclosure.

Maintaining airway patency refers to controlling the contraction and relaxation states of at least one of the muscles that controls the motion of an individual's tongue and innervated by the hypoglossal nerve, for example, the genioglossus muscle, the hyoglossus muscle, the digastric anterior muscle, the mylohyoid muscle, the geniohyoid muscle, the styoglossus muscle, the superior longitudinal muscle, the inferior longitudinal muscle, the transverse muscle, the vertical muscle, or a combination thereof, to sustain the individual's ability to inhale oxygen and exhale carbon dioxide. Optionally, without activating the other pairs of extrinsic muscles of the tongue.

Methods according to the present disclosure may decrease snoring by, for example, increasing the amount of air and/or oxygen passing through an individual's airway, increasing the size of an individual's airway opening, decreasing and/or clearing a blockage or obstruction in an individual's airway, or a combination thereof. In some examples according to the present disclosure, decreasing snoring may result in a decrease of about 10%, about 25%, about 50%, about 75%, about 80%, about 85%, about 90%, about 95%, or 100% from the decibel level of snoring before stimulating at least four regions of the individual's neck according to the present disclosure.

Methods according to the present disclosure may decrease the incidence of obstructive sleep apnea by, for example, increasing the amount of air and/or oxygen passing through an individual's airway, increasing the size of an individual's airway opening, decreasing and/or clearing a blockage or obstruction in an individual's airway, or a combination thereof. In some examples according to the present disclosure, decreasing the incidence of obstructive sleep apnea may result in a decrease of the incidence of obstructive sleep apnea of an individual by about 10%, about 25%, about 50%, about 75%, about 80%, about 85%, about 90%, about 95%, or 100% compared to the incidence of obstructive sleep apnea of the individual before stimulating at least four regions of the individual's neck according to the present disclosure.

Stimulating an individual's neck refers to providing any type of stimulant, for example an electrical impulse, that causes a muscle contraction of the individual. Optionally, the muscle contraction is the contraction of at least one of the muscles that controls the motion of an individual's tongue and innervated by the hypoglossal nerve, for example, the genioglossus muscle, the hyoglossus muscle, the digastric anterior muscle, the mylohyoid muscle, the geniohyoid muscle, the styoglossus muscle, the superior longitudinal muscle, the inferior longitudinal muscle, the transverse muscle, the vertical muscle, or a combination thereof. Optionally, the muscle contraction is a contraction of the genioglossus muscle.

Regions of an individual's neck refers to areas on the surface of the individual's neck region that are, independently, of sufficient size and at a sufficient location that when stimulated, result in the contraction of at least one of the individual's muscles that controls the motion of an individual's tongue and innervated by the hypoglossal nerve, for example, the genioglossus muscle, the hyoglossus muscle, the digastric anterior muscle, the mylohyoid muscle, the geniohyoid muscle, the styoglossus muscle, the superior longitudinal muscle, the inferior longitudinal muscle, the transverse muscle, the vertical muscle, or a combination thereof. The size of the regions may be from about 75 mm$^2$ to about 700 mm$^2$. Optionally, the regions may have a radius from about 5 mm to about 15 mm. Regions smaller than about 75 mm$^2$ may: (1) provide an insufficient intensity of electrical stimulation to cause contraction of the muscles that control the motion of an individual's tongue without causing skin tissue burns in the area of stimulation; (2) increase the likelihood of misaligning the regions of stimulation causing the stimulation to be insufficient; (3) increasing the stimulation density while keeping the intensity constant resulting in burning the contact skin; (4) or a combination thereof. Regions larger than about 700 mm$^2$ may stimulate muscles other than the individual's muscles that control the motion of an individual's tongue and innervated by the hypoglossal nerve resulting in facial twitching and/or facial muscle spasms and/or blocking or inhibiting the individual's ability to enter into low wave and/or rapid eye movement sleep, or a combination thereof.

The presently disclosed methods comprise a step of stimulating at least four regions of an individual's neck. Optionally, two of the at least four regions of the individual's neck are anterior triangle regions on opposing sides of the individual's midline, and another two of the at least four regions of the individual's neck are anterior triangle regions on opposing sides of the individual's midline, posterior to the two of the at least four regions. The anterior triangle region refers to a region bounded by inferior mandible, anterior border of the sternocleidomastoid, and anterior the midline of the neck. A skilled person would likely consider that stimulating only one region of an individual's neck would be sufficient to cause contraction of the muscles that control the motion of an individual's tongue and are innervated by the hypoglossal nerve, to cause an increase of air and/or oxygen to pass through the individual's airway, increase the size of an individual's airway opening, decreasing and/or clearing a blockage or obstruction in an individual's airway, or a combination thereof. However, surprisingly, the inventors found that simulating only one side of the individual's midline may cause the individual's tongue to move to one side and cause partial blockage of the individual's airway. Such a blockage may increase snoring, as described in Example 1. Furthermore, a skilled person would likely consider that stimulating only two regions of an individual's neck, one on either side of the individual's midline, would be sufficient to cause contraction of the muscles that control the motion of an individual's tongue and are innervated by the hypoglossal nerve, to cause an increase of air and/or oxygen to pass through the individual's airway, increase the size of an individual's airway opening, decreasing and/or clearing a blockage or obstruction in an individual's airway, or a combination thereof. However, surprisingly, the inventors found that stimulating only one region on both sides of an individual's midline may cause the current to travel in the coronal plane stimulating muscles and/or nerves other than those muscles and/or nerves that control the motion of the individual's tongue, which may result in insufficient stimulation to cause contraction of the muscles that control the motion of the individual's tongue, as described in Example 2.

Optionally, two of the at least four regions are submental triangle regions and/or submandibular triangle regions, and the another two of the at least four regions may be submental triangle regions and/or submandibular triangle regions. Optionally, two of the at least four regions of an individual's neck are submental triangle regions on opposing sides of the individual's midline, and another two of the at least four regions of the individual's neck are submandibular regions on opposing sides of the individual's midline. The submental triangle regions refers to a region located between the body of the hyoid bone and right and left anterior bellies of the digastric muscles. The submandibular triangle region refers to a region located between inferior the mandible and anterior and posterior the bellies of the digastric muscles.

Optionally, two of the at least four regions of an individual's neck are a pair of first regions of the individual's hypoglossal nerves and the another two of the at least four regions of the individual's neck are a pair of second regions of the individual's pair of hypoglossal nerves, the pair of second regions being anterior to the pair of first regions. Optionally, each of the pair of first regions is, independently, positive or negative, and each of the pair of second regions is, independently, positive or negative. Optionally, where one of the pair of first regions is positive, the second region that is on the same side of the midline as the one of the pair of first regions is negative. Optionally, where one of the pair of first regions is negative, the second region that is on the same side of the midline as the one of the pair of first regions is positive. The hypoglossal nerves arise from the hypoglossal nucleus in the medulla oblongata of the brain, exit the cranium via the hypoglossal canal, and travel between the carotid artery and jugular vein to end up on the underside of the tongue. The hypoglossal nerves split into a lateral and medial contingent. The medial contingent splits into several branches that enter the horizontal and oblique compartments of the muscles that control the motion of an individual's tongue. The distance between the first regions of the hypoglossal nerves and the pair of second regions of the hypoglossal nerves may be from about 1.0 cm to about 3.0 cm, for example, 1.0 cm, 1.5 cm, 2.0 cm, 2.5 cm, 3.0 cm, or the distance is from one of the distances listed above to any one of the other distances listed above, or any distance therebetween. Optionally, the pair of first regions and the pair of second regions of the hypoglossal nerves are stimulated directly, for example, electric current is passed through an individual's skin, for example, transcutaneously, directly to the pair of first regions and the pair of second regions of the hypoglossal nerves. Alternatively, the pair of first regions and the pair of second regions of the hypoglossal nerves are stimulated indirectly, for example, electric current is passed through an individual's skin, for example, transcutaneously, indirectly to the pair of first regions and the pair of second regions of the hypoglossal nerves. In some examples according to the present disclosure where the stimulation is indirect, electric current is passed through an individual's skin to the pair of first regions and the pair of second regions of the hypoglossal nerves through intervening facial tissue.

Optionally, the pair of first regions of the hypoglossal nerves is a pair of regions anterior of the point where the hypoglossal nerves split between a medial contingent and a lateral contingent. Optionally, the pair of first regions of the hypoglossal nerves is the medial contingent. Optionally, the pair of second regions of the hypoglossal nerves is a pair of regions posterior of the point where the hypoglossal nerves split between a medial contingent and a lateral contingent. Optionally, the pair of second regions of the hypoglossal nerves is the medial contingent.

Electrical impulses that cause the contraction of at least one of the muscles that controls the motion of an individual's tongue and innervated by the hypoglossal nerve may comprise passing an electric current between: 1) at least two regions of the individual's anterior triangle regions on opposing sides of the individual's midline; and 2) at least another two regions of the individual's anterior triangle regions on opposing sides of the individual's midline, where the current passes between the at least two regions and the another two regions located on the same side of the individual's midline. Optionally, the electric current is passed from the at least two regions of an individual's anterior triangle regions on opposing sides of the individual's midline to the at least another two regions of the individual's anterior triangle regions on opposing sides of the individual's midline, where the current passes from the at least two regions to the another two regions located on the same side of the individual's midline.

The electric current may be produced by any at least two types of waveform modulations provided that the resulting stimulation at at least four regions of the individual's neck according to the present disclosure causes contraction of at least one of the muscles that controls the motion of an individual's tongue and innervated by the hypoglossal nerve, for example, the genioglossus muscle, the hyoglossus muscle, the digastric anterior muscle, the mylohyoid muscle, the geniohyoid muscle, the styoglossus muscle, the superior longitudinal muscle, the inferior longitudinal muscle, the transverse muscle, the vertical muscle, or a combination thereof. Optionally, the stimulation: (1) does not cause contractions of muscles other than the muscles that control the motion of the individual's tongue and innervated by the hypoglossal nerve; (2) avoids activating facial nerves; or (3) a combination thereof.

At least two waveforms may be required to sufficiently stimulate the efferent nerve fiber to activate at least one of the muscles that controls the motion of an individual's tongue and innervated by the hypoglossal nerve, for example when decreasing the risk of triggering the cutaneous afferents is desirable. Methods that utilize less than two types of waveforms may not be able to achieve tetanic contraction of at least one of the muscles that controls the motion of an individual's tongue and innervated by the hypoglossal nerve within the phasic movement, which may result in activating unintentional muscles causing facial twitches, an insufficient amount of movement of an individual's tongue, or ionization of the nerve.

Optionally, at least a first type of the at least two types of waveform modulations is a low-intensity, high frequency waveform and another type of the at least two types of waveform modulations is a high-intensity, low-frequency waveform.

The high-intensity, low-frequency waveform may comprise at least two pulses. The number of at least two pulses may vary provided that the resulting stimulation at at least four regions of the individual's neck according to the present disclosure causes contraction of at least one of the muscles that controls the motion of an individual's tongue and innervated by the hypoglossal nerve, for example, the genioglossus muscle, the hyoglossus muscle, the digastric anterior muscle, the mylohyoid muscle, the geniohyoid muscle, the styoglossus muscle, the superior longitudinal muscle, the inferior longitudinal muscle, the transverse muscle, the vertical muscle, or a combination thereof. Optionally, the stimulation: (1) does not cause contractions of muscles other than the muscles that control the motion of the tongue and innervated by the hypoglossal nerve; (2) avoids activating facial nerves; or (3) a combination thereof. Optionally, one of the at least two pulses is positive in magnitude and another pulse of the at least two pulses is negative in magnitude.

The low-intensity, high-frequency waveform may comprise at least two pulses. The number of at least two pulses may vary provided that the resulting stimulation at at least four regions of the individual's neck according to the present disclosure causes contraction of at least one of the muscles that controls the motion of an individual's tongue and innervated by the hypoglossal nerve, for example, the genioglossus muscle, the hyoglossus muscle, the digastric anterior muscle, the mylohyoid muscle, the geniohyoid muscle, the styoglossus muscle, the superior longitudinal muscle, the inferior longitudinal muscle, the transverse muscle, the vertical muscle, or a combination thereof. Optionally, the stimulation: (1) does not cause contractions of muscles other than the muscles that control the motion of the tongue and innervated by the hypoglossal nerve; (2) avoids activating facial nerves; or (3) a combination thereof. Optionally, one of the at least two pulses is positive in magnitude and another pulse of the at least two pulses is negative in magnitude. The low-intensity, high-frequency waveform may be a pulsed waveform and/or a burst waveform. The pulsed waveform may comprise from about 1 to about 5 pulses per second and a pulse width from about 100 to about 300 µs. The burst waveform may comprise from about 1 to about 5 bursts per second, each burst comprises from about 40 to about 100 pulses per second, and a pulse width from about 100 to about 300 µs. The pulsed waveform may be biphasic pulsed waveform and/or the burst waveform may be biphasic burst waveform, for example when deceasing the risk of ion accumulation at the regions of stimulation is desired.

The pulses may have any frequency provided that the resulting stimulation at at least four regions of the individual's neck according to the present disclosure causes contraction of at least one of the muscles that controls the motion of an individual's tongue and innervated by the hypoglossal nerve, for example, the genioglossus muscle, the hyoglossus muscle, the digastric anterior muscle, the mylohyoid muscle, the geniohyoid muscle, the styoglossus muscle, the superior longitudinal muscle, the inferior longitudinal muscle, the transverse muscle, the vertical muscle, or a combination thereof. Optionally, the stimulation: (1) does not cause contractions of muscles other than the muscles that control the motion of the tongue and innervated by the hypoglossal nerve; (2) avoids activating facial nerves; or (3) a combination thereof. The high-intensity, low-frequency waveform pulse frequency may be, independently, from about 1 Hz to about 20 Hz, for example, about 1 Hz; about 2 Hz; about 3 Hz; about 4 Hz; about 5 Hz; about 6 Hz; about 7 Hz; about 8 Hz; about 9 Hz; about 10 Hz; about 11 Hz; about 12 Hz; about 13 Hz; about 14 Hz; about 15 Hz; about 16 Hz; about 17 Hz; about 18 Hz; about 19 Hz; about 20 Hz; or the frequency is from one of the frequencies listed above to any one of the other frequencies listed above, or any frequency therebetween. A pulse frequency that is less than 1 Hz may increase the time in between each pulse and provide more time for the muscle to relax, which may cause blockage of the airway. In some examples according to the present disclosure, the pulse frequency is the combination of the high-intensity, low-frequency waveform with low-intensity high-frequency waveforms in-between. The combination of the high-intensity, low-frequency waveform and the low-intensity, high-frequency waveforms may stimulate the deeply embedded hypoglossal nerve while maintaining the contraction of the muscles innervated by the hypoglossal nerve for a sustained period of time, improving the performance of the stimulation. The low-intensity, high-frequency waveform pulse frequency may be, independently, from about 10 Hz to about 100 Hz, for example, about 10 Hz; about 20 Hz; about 25 Hz; about 30 Hz; about 35 Hz; about 40 Hz; about 45 Hz; about 50 Hz; about 55 Hz; about 60 Hz; about 65 Hz; about 70 Hz; about 75 Hz; about 80 Hz; about 85 Hz; about 90 Hz; about 95 Hz; about 100 Hz or the frequency is from one of the frequencies listed above to any one of the other frequencies listed above, or any frequency therebetween.

The pulse width of the pulses may vary provided that the resulting stimulation at at least four regions of the individual's neck according to the present disclosure causes contraction of at least one of the muscles that controls the motion of an individual's tongue and innervated by the hypoglossal nerve, for example, the genioglossus muscle, the hyoglossus muscle, the digastric anterior muscle, the mylohyoid muscle, the geniohyoid muscle, the styoglossus muscle, the superior longitudinal muscle, the inferior longitudinal muscle, the transverse muscle, the vertical muscle, or a combination thereof. Optionally, the stimulation: (1) does not cause contractions of muscles other than the muscles that control the motion of the tongue and innervated by the hypoglossal nerve; (2) avoids activating facial nerves; or (3) a combination thereof. The pulse width may be from about 100 µs to about 400 µs, for example, about 100 µs, about 125 µs, about 150 µs, about 175 µs, about 200 µs, about 225 µs, about 250 µs, about 275 µs, about 300 µs, about 325 µs, about 350 µs, about 375 µs, about 400 µs; or the pulse width is from one of the widths listed above to any one of the other widths listed above, or any width therebetween. A pulse width that is less than 100 µs may not be sufficiently long to fully activate the nerve. A pulse width that is more than 400 µs may cause skin burn and/or muscle fatigue, which may delay the response time the muscle has to the stimulation.

The duty cycle of the electric current may be any amount of time provided that the resulting stimulation at at least four regions of the individual's neck according to the present disclosure causes contraction of at least one of the muscles that controls the motion of an individual's tongue and innervated by the hypoglossal nerve, for example, the genioglossus muscle, the hyoglossus muscle, the digastric anterior muscle, the mylohyoid muscle, the geniohyoid muscle, the styoglossus muscle, the superior longitudinal muscle, the inferior longitudinal muscle, the transverse muscle, the vertical muscle, or a combination thereof. Optionally, the stimulation: (1) does not cause contraction of muscles other than the genioglossus muscles; (2) avoids activating facial nerves; or (3) a combination thereof. The duty cycle may be from about 0.25% to about 1.0%, for example, 0.25%; 0.30%, 0.40%, 0.50%, 0.60%, 0.70%, 0.75%, 1.0%; or the duty cycle is from one of the percentages listed above to any one of the other percentages listed above, or any percentage therebetween. A duty cycle that is less than 0.25% may provide insufficient stimulation to contract at least one of the muscles innervated by the hypoglossal nerve. A duty cycle that is greater than 1.0% may: increase the risk of causing genioglossus muscle fatigue, increase the risk of damage of the lingual tongue muscle, increase pharyngeal stiffness, or a combination thereof. Optionally, the duty cycle is about 1.0%, for example when decreasing the risk of pharyngeal stiffness, genioglossal muscle fatigue, or a combination thereof, is desirable.

The amount of electric current may vary provided that the resulting stimulation at at least four regions of the individual's neck according to the present disclosure causes contraction of at least one of the muscles that controls the motion of an individual's tongue and innervated by the hypoglossal nerve, for example, the genioglossus muscle, the hyoglossus muscle, the digastric anterior muscle, the mylohyoid muscle, the geniohyoid muscle, the styoglossus muscle, the superior longitudinal muscle, the inferior longitudinal muscle, the transverse muscle, the vertical muscle, or a combination thereof. Optionally, the stimulation: (1) does not cause contractions of muscles other than the muscles that control the motion of the tongue and innervated by the hypoglossal nerve; (2) avoids activating facial nerves; or (3) a combination thereof. The amount of current may be from about 1 milliampere (mA) to about 33 mA, for example, about 1 mA; about 2 mA; about 3 mA; about 4 mA; about 5 mA; about 10 mA; about 15 mA; about 20 mA; about 25 mA; about 30 mA; about 33 mA; or the amount of current is from one of the milliamperes listed above to any one of the other milliamperes listed above, or any milliampere therebetween. A pulse width that is less than 1 mA may not sufficiently stimulate the hypoglossal nerve to contract the genioglossus muscle. A pulse width that is greater than 33 mA may burn an individual's skin tissue that is conducting the current, cause visible facial muscle twitching, or a combination thereof. Optionally, the amount of current from about 10 mA to about 22 mA, for example when decreasing the risk of burning an individual's skin that is conducting the current and increasing the efficiency of triggering the hypoglossal nerve is desirable.

Optionally, the method further comprises a step of calibration. The calibration step may comprise a step of stimulating the at least four regions of an individual's neck with increasing increments of stimulation intensity until a threshold is met. The threshold may be: (1) when the individual feels discomfort; (2) when the current stimulation reaches harmful levels; (3) a pre-set value; or (4) a combination thereof. Optionally, when the threshold is met, the stimulation intensity may decrease in increments of stimulation.

Optionally, stimulating at least four regions of an individual's neck is provided by a device comprising at least four stimulators and at least one processor in electrical communication with the at least four stimulators to control the stimulation. In the context of the present disclosure, the phrase "electrical communication" means that electrons are transferable between the recited components. Optionally, components that are in "electrical communication" are connected by an electrically conductive material, for example, a copper material.

The stimulators are any type of transcutaneous stimulators that are able to provide stimulation at at least four regions of the individual's neck according to the present disclosure that causes contraction of at least one of the muscles that controls the motion of an individual's tongue and innervated by the hypoglossal nerve, for example, the genioglossus muscle, the hyoglossus muscle, the digastric anterior muscle, the mylohyoid muscle, the geniohyoid muscle, the styoglossus muscle, the superior longitudinal muscle, the inferior longitudinal muscle, the transverse muscle, the vertical muscle, or a combination thereof. Optionally, the stimulation: (1) does not cause contractions of muscles other than the muscles that control the motion of the tongue and innervated by the hypoglossal nerve; (2) avoids activating facial nerves; or (3) a combination thereof. Optionally, the stimulators are electrodes.

The stimulators are made of any conductive material that has high conductivity, low resistance, relatively inert/low reactivity with skin, or a combination thereof. Optionally, the stimulators are gold-plated copper electrodes, copper plated/sheets, silver plated/sheets, gold plated/sheets, silver chloride paste, laser-printed silver deposit, or a combination thereof. Optionally, the stimulators are gold-plated copper and/or silver-plated copper, for example when the decreasing the cost and/or difficulty of manufacturing is desirable. Optionally, the stimulators are gold-plated copper, for example when increased inert properties, decreased reactivity with skin, or a combination thereof is desirable. Optionally, the stimulators are silver-plated copper, for example when increased resilience and resistance to degradation, for example from oils and sweat from skin of an individual, is desirable.

The size and shape of the stimulators may vary provided that the resulting stimulation at at least four regions of the individual's neck according to the present disclosure causes contraction of at least one of the muscles that controls the motion of an individual's tongue and innervated by the hypoglossal nerve, for example, the genioglossus muscle, the hyoglossus muscle, the digastric anterior muscle, the mylohyoid muscle, the geniohyoid muscle, the styoglossus muscle, the superior longitudinal muscle, the inferior longitudinal muscle, the transverse muscle, the vertical muscle, or a combination thereof. Optionally, the stimulation: (1) does not cause contractions of muscles other than the muscles that control the motion of the tongue and innervated by the hypoglossal nerve; (2) avoids activating facial nerves; or (3) a combination thereof. Optionally, the stimulators or electrodes range in size from about 75 mm$^2$ to about 700 mm$^2$. Stimulator sizes that are less than about 75 mm$^2$ may: (1) provide an insufficient intensity of electrical stimulation to cause contraction of the muscles that control the tongue motion of an individual's tongue without causing skin tissue burns in the area of stimulation; (2) increase the likelihood of misaligning the stimulators causing the stimulation to be insufficient; (3) increase the stimulation density while keeping the intensity constant may burn the contact skin; (4) or a combination thereof. Stimulator sizes that are greater than about 700 mm$^2$ may stimulate muscles other than an individual's muscles that control the tongue motion of the individual's tongue and innervated by the hypoglossal nerve resulting in facial twitching, facial muscle spasms, blocking or inhibiting the individual's ability to enter into slow wave and/or rapid eye movement, or a combination thereof. Optionally, the stimulators are circular, square, or oval in shape.

The shape of the device may vary provided that the stimulators are orientated to provide stimulation to at least four regions of an individual's neck, where two of the at least four regions of the individual's neck are anterior triangle regions on opposing sides of the individual's midline, and another two of the at least four regions of the individual's neck are anterior triangle regions on opposing sides of the individual's midline, posterior to the two of the at least four regions. Optionally, the device has an L-shaped body or a V-shaped body comprising a first stem and a second stem, the first stem comprising two of the at least four stimulators for stimulating two of the at least four regions of an individual's neck on one side of the individual's midline, the second stem comprising another two of the at least four stimulators for stimulating another two of the at least four regions of the individual's neck on the second side of the individual's midline.

Figure 1B:
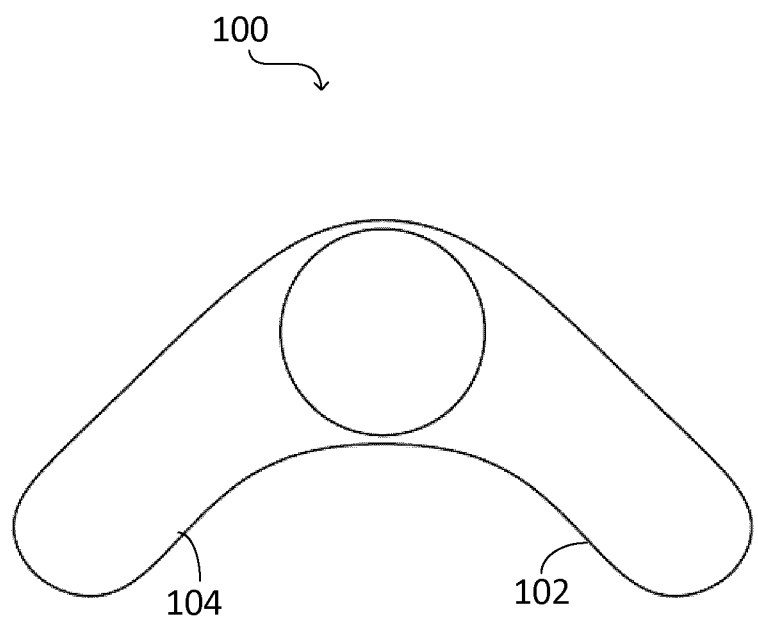

FIGS. 1A and B illustrate one example of a device according to the present disclosure in top view (FIG. 1A) and bottom view (FIG. 1B). The device (100) has an L-shaped body comprising a first stem (102) and a second stem (104), the first stem (102) comprising two stimulators (106a; 106b) for stimulating two regions of an individual's neck on one side of the individual's midline, the second stem (104) comprising another two stimulators (106c; 106d) for stimulating another two regions of the individual's neck on the second side of the individual's midline.

The device is constructed of any material that is couplable to the at least four stimulators and orients the position of the stimulators for stimulating the at least four regions of the individual's neck. Optionally, the device is constructed of material that is sufficiently flexible to orient the stimulators for stimulating the at least four regions of the individual's neck. Optionally, the device is constructed of thermoplastic elastomer and/or Liquid Silicone Rubber.

The herein described device may be removably couplable to an individual's neck using any type of removable akin adhesive that sufficiently couples the herein described device to an individual's neck to allow the at least four stimulators to stimulate the at least four regions of the individual's neck, preferably while the individual is sleeping. The adhesive may be composed of synthetic rubber, natural rubber, latex, silicone, acrylic, acrylate, hydrocolloids, and/or hydrogel. The adhesive may be biocompatible, for example, a medical-grade skin adhesive. In some examples according to the present disclosure, the adhesive is a double-coated tape. The adhesive may adhere to steel at from about 1 g/25 mm width to about 3000 g/25 mm width. At least a portion of the adhesive may have a conductivity from about 0 to about 10,000 ohm-cm. In some examples according to the present disclosure, the adhesive has a total thickness from about 0.001 mm to about 3 mm. The skin adhesive may be XTRATA PERME-ROLL AIR using STRATEAGEL or Yuki-gel adhesive from Nitto Denko Corporation.

Optionally, the device is couplable to hydrogel that conducts electrical signals from at least a portion of the at least four stimulators to an individual's neck. The hydrogel may be any polymer network that is composed of absorbent hydrophilic polymer chains. The hydrogel may be in a liquid form, or a gel form, and the former may be conductive form, or non-conductive. Optionally, the hydrogel may be produced with an inherent skin adhesive property, for example, silicon or another insulator can be added as a hydrogel component to increase the density and decrease conductivity of the resulting hydrogel. Alternatively, the hydrogel may be bonded to a skin adhesive during manufacturing. The hydrogel may be bonded to a skin adhesive via heat, compression, or a combination of heat and compression, which catalyzes the natural adhesive properties of both components. Optionally, the hydrogel and the skin adhesive may be bonded via another chemical adhesive, or by sandwiching a layer of hydrogel between two layers of the skin tape, or sandwiching the main skin-tape component between two layers of hydrogel in each of the four hydrogel locations by making the hydrogel components slightly larger than the holes in the skin-tape. Once the single-piece adhesive pad is created by bonding the skin-tape and the hydrogel, the single piece may be coupled in place to a device according to the present disclosure by the adhesive properties of both the hydrogel and the skin tape, for example, the skin tape may be a double-sided adhesive component which has STRATAGEL on one side, and an adhesive on the other which has been selected for the material of the body of the herein described device. The hydrogel may have hypoallergenic and/or biocompatible properties. In some examples according to the present disclosure, the hydrogel may be M863X Promeon Hi-Adhesion Gel from R&D Medical, or M807 Comfort Gel A from R&D Medical.

The orientation of the hydrogel coupled to the herein described device may allow electrical current to pass from, independently, the stimulators to an individual's neck. Optionally, the orientation of the hydrogel coupled to the herein described device may allow electrical current to pass from, independently, a portion of the stimulators to an individual's neck and disallow electrical current to pass from another portion of the stimulators to the individual's neck. Accordingly, the orientation of the hydrogel coupled to the herein described device may be adjusted to accommodate different sizes, structures, and/or contours of individuals' necks and provide stimulation to at least two regions of each individual's neck that are anterior triangle regions on opposing sides of the individual's midline, and another at least two regions of the individual's neck that are anterior triangle regions on opposing sides of the individual's midline, posterior to the at least two regions. Optionally, the orientation of the hydrogel coupled to the herein described device allows electrical current to pass from the entirety of the stimulators to an individual's neck.

The presently disclosed method may use the presently disclosed device to: (1) increase the amount of air and/or oxygen passing through the airway of an individual; (2) reduce airway restrictions in an individual; (3) increase airway patency and/or maintaining airway patency in an individual; (4) decrease snoring, obstructive sleep apnea, or a combination thereof in an individual; or (5) a combination thereof.

The presently disclosed devices may be incorporated into a system to: (1) increase the amount of air and/or oxygen passing through the airway of an individual; (2) reduce airway restrictions in an individual; (3) increase airway patency and/or maintaining airway patency in an individual; (4) decrease snoring, obstructive sleep apnea, or a combination thereof in an individual; or (5) a combination thereof.

The system may comprise: the presently disclosed device and a power source coupled to the device for providing an electrical signal to the at least four stimulators of the device. The power source may comprise a battery, a digital to analog converter, a direct current to direct current boost converter, or a combination thereof. The battery may be a LiFePO4 material Li-Polymer battery. The digital to analog converter may be DAC70508ZRTET—manufactured by Texas Instruments. The direct current to direct current boost converter may be TPS61280D manufactured by Texas instruments. Optionally, the device may be in wireless communication with a user interface that controls the stimulation parameters. Optionally, the power source is mounted on the device, for example, a LiFePO4 battery.

The device according to the present disclosure may comprise an additional sleep sensor, for example, a sensor to track sleep stages, apnea events, hypoxia, blood pressure, an accelerometer, a reflective blood oximeter, a heart rate monitor, a microphone, or a combination thereof. Optionally, the additional sleep sensor is an accelerometer, blood oximeter, heart rate monitor, microphone, ultrawideband radar sensor, or a combination thereof. Optionally, the accelerometer, blood oximeter, and heart rate monitor are attached to the device for example, mounted on the device. Optionally, the microphone is attached to the device or is located remotely from the device and in electrical and/or wireless communication with the device. Optionally, the ultrawideband radar sensor is located remotely from the device and in electrical and/or wireless communication with the device. A skilled person would understand that the herein described additional sleep sensors may have components that are mounted on the device and components that are located remotely from the device and in electrical and/or wireless communication with the device.

The herein described devices and methods may be used to detect when one of the individual's muscles that controls the motion of the individual's tongue and innervated by the hypoglossal nerve, for example, the genioglossus muscle, the hyoglossus muscle, the digastric anterior muscle, the mylohyoid muscle, the geniohyoid muscle, the styoglossus muscle, the superior longitudinal muscle, the inferior longitudinal muscle, the transverse muscle, the vertical muscle, or a combination thereof, is relaxing, and the individual has started snoring or has not yet started snoring but the individual's muscle has relaxed to the extent that is measurable by external or internal measurements, for example, using the herein described additional sensors. At this point where the muscle is relaxed to this extent, the herein described device and method may be used to detect a change in airway patency or reduction of oxygen passing through the airway or a reduction of airway restrictions, and the herein described device or method may stimulate at least four regions of the individual's neck according to the present disclosure to activate said muscle.

Figure 2:
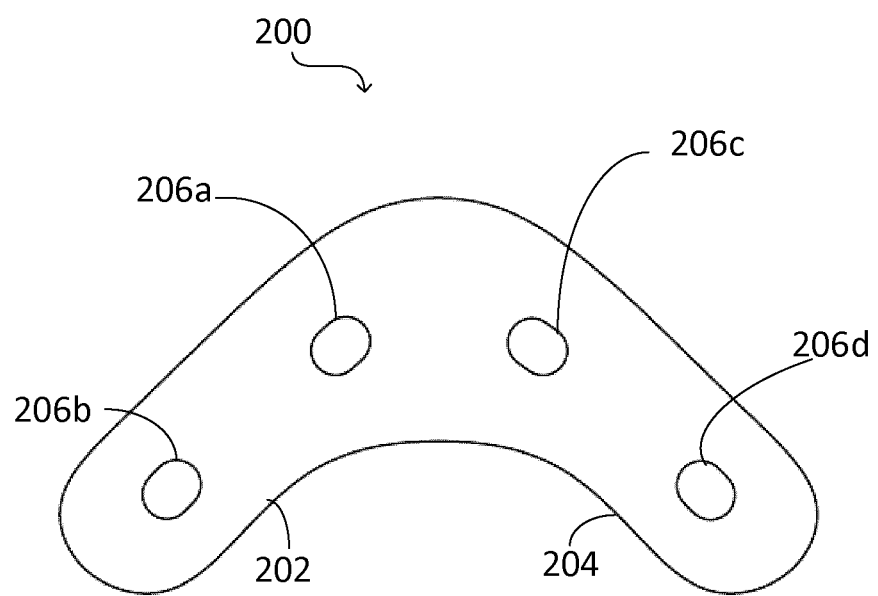
FIG. 2 is an illustration of a removable adhesive according to the present disclosure that is couplable to the device illustrated in FIGS. 1A and B.

FIG. 2 illustrates an adhesive according to the present disclosure that is couplable to the device illustrated in FIGS. 1A and B. The adhesive (200) has an L-shaped shaped body comprising a first adhesive stem (202) and a second adhesive stem (204), the first adhesive stem (202) comprising two hydrogel regions (206a; 206b) that, when coupled to the device illustrated in FIGS. 1A and B, are in electrical communication with at least a portion of the stimulators 106a and 106b, respectively. The second adhesive stem (204) comprises another two hydrogel regions (206c; 206d) that, when coupled to the device illustrated in FIGS. 1A and B, are in electrical communication with at least a portion of stimulators 106c and 106d, respectively.

Figure 3:
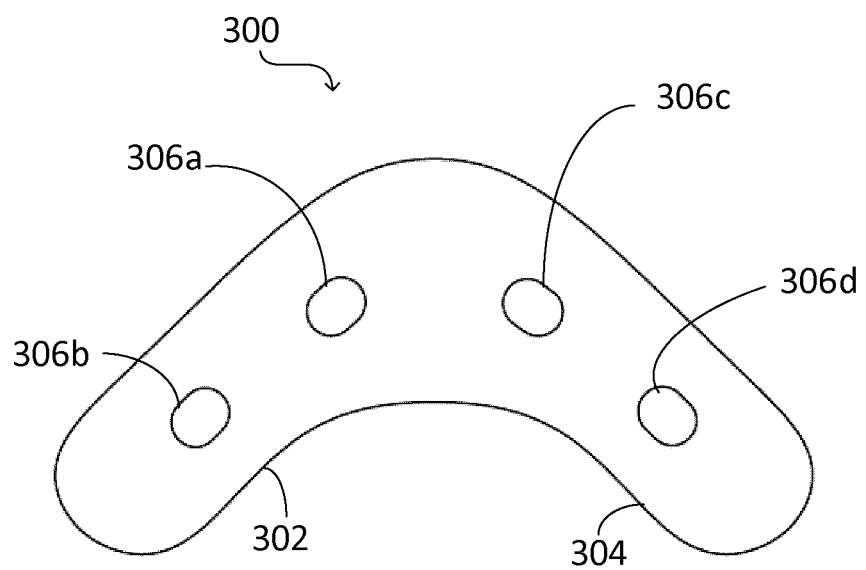
FIG. 3 is an illustration of another removable adhesive according to the present disclosure that is couplable to the device illustrated in FIGS. 1A and B.

FIG. 3 illustrates an adhesive according to the present disclosure that is couplable to the device illustrated in FIGS. 1A and B. The adhesive (300) has an L-shaped shaped body comprising a first adhesive stem (302) and a second adhesive stem (304), the first adhesive stem (302) comprising two hydrogel regions (306a; 306b) that, when coupled to the device illustrated in FIGS. 1A and B, are in electrical communication with at least a portion of the stimulators (106a and 106b), respectively. The second adhesive stem (304) comprises another two hydrogel regions (306c; 306d) that, when coupled to the device illustrated in FIGS. 1A and B, are in electrical communication with at least a portion of stimulators 106c and 106d, respectively.

Figure 4:
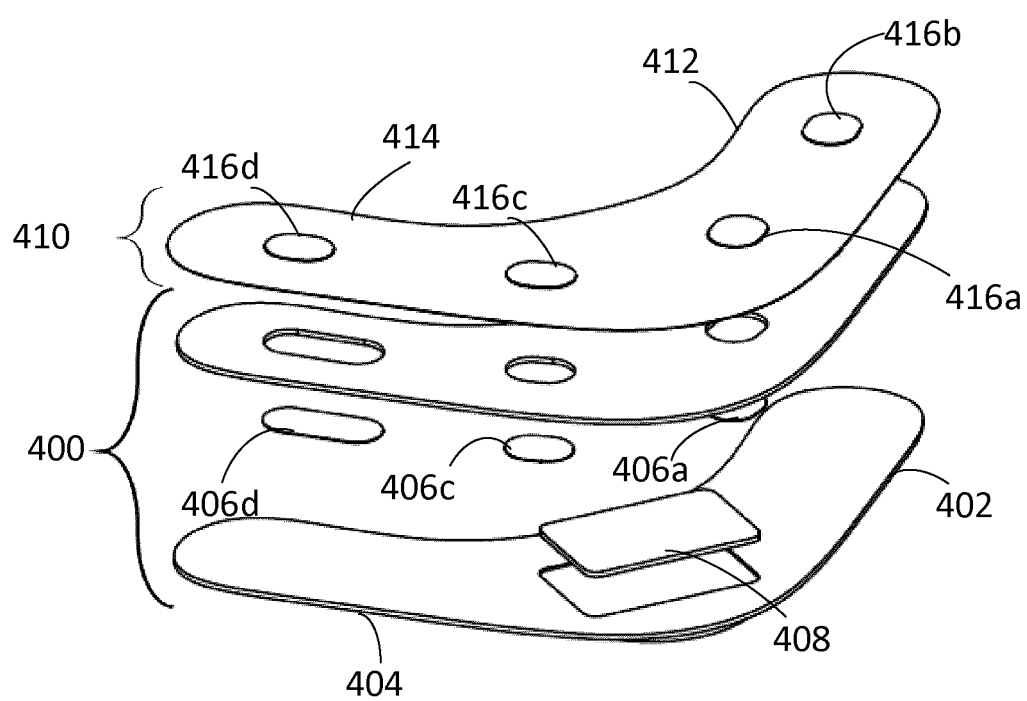
FIG. 4 is an illustration of the device illustrated in FIGS. 1A and B coupled to removable adhesive according to the present disclosure in an exploded view.

FIG. 4 illustrates a device according to the present disclosure coupled to an adhesive according to the present disclosure in an exploded view. The device (400) has an L-shaped body comprising a first stem (402) and a second stem (404), the first stem (402) comprising two stimulators (406a; not shown) for stimulating two regions of an individual's neck on one side of the individual's midline, the second stem (404) comprising another two stimulators (406c; 406d) for stimulating another two regions of the individual's neck on the second side of the individual's midline. The device also comprises electronics (408) in electrical communication with the four stimulators to control the electrical stimulation, the electronics (408), including a processor, for processing, managing power, and generating waveforms. The adhesive (410) has an L-shaped shaped body comprising a first adhesive stem (412) and a second adhesive stem (414), the first adhesive stem (412) comprising two hydrogel regions (416a; 416b) that, when coupled to the device (400), are in electrical communication with at least a portion of the stimulators (406a and not shown), respectively. The second stem (414) comprises another two hydrogel regions (416c; 416d) that, when coupled to the device (400), are in electrical communication with at least a portion of stimulators 406c and 406d, respectively.

Figure 5:
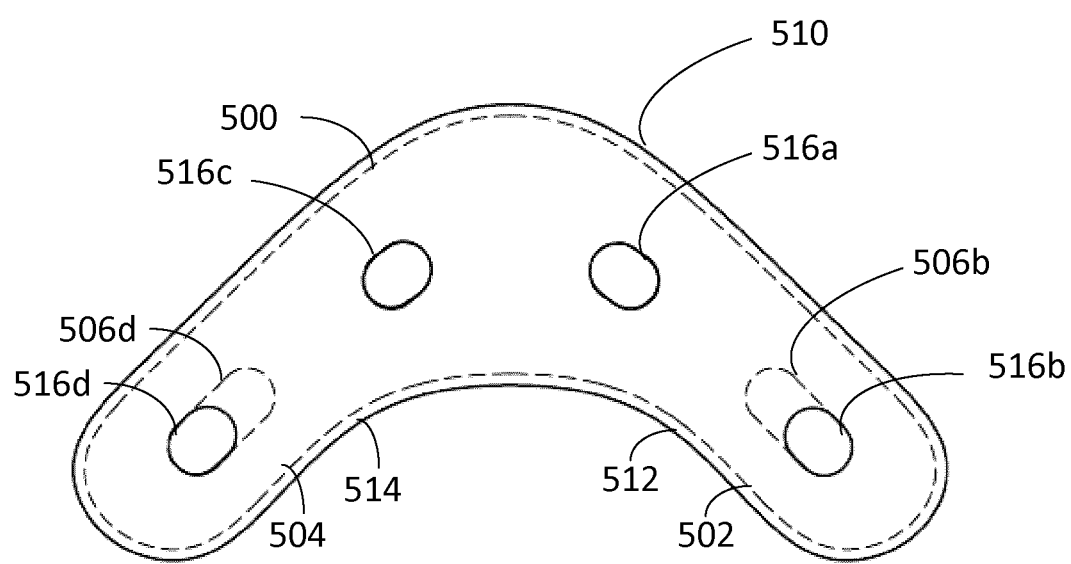
FIG. 5 is an illustration of the device illustrated in FIGS. 1A and B coupled to the removable adhesive illustrated in FIG. 2 in bottom view. The device is represented by dotted lines.

FIG. 5 illustrates a device according to the present disclosure coupled to an adhesive according to the present disclosure in a bottom view. The device (500; dotted lines) has an L-shaped body comprising a first stem (502) and a second stem (504), the first stem (502) comprising two stimulators (not shown; 506b) for stimulating two regions of an individual's neck on one side of the individual's midline, the second stem (504) comprising another two stimulators (not shown; 506d) for stimulating another two regions of the individual's neck on the second side of the individual's midline. The adhesive (510) has an L-shaped shaped body comprising a first adhesive stem (512) and a second adhesive stem (514), the first adhesive stem (512) comprising two hydrogel regions (516a; 516b). When coupled to the device (500), hydrogel region (516a) is in electrical communication with a stimulator (now shown) in its entirety, and hydrogel region (516b) is in electrical communication with a portion of stimulator (506b). The second stem (514) comprises another two hydrogel regions (516c; 516d). When coupled to the device (500), hydrogel region 516c is in electrical communication with a stimulator (now shown) in its entirety, and hydrogel region 516d is in electrical communication with a portion of stimulator (506d).

Figure 6:
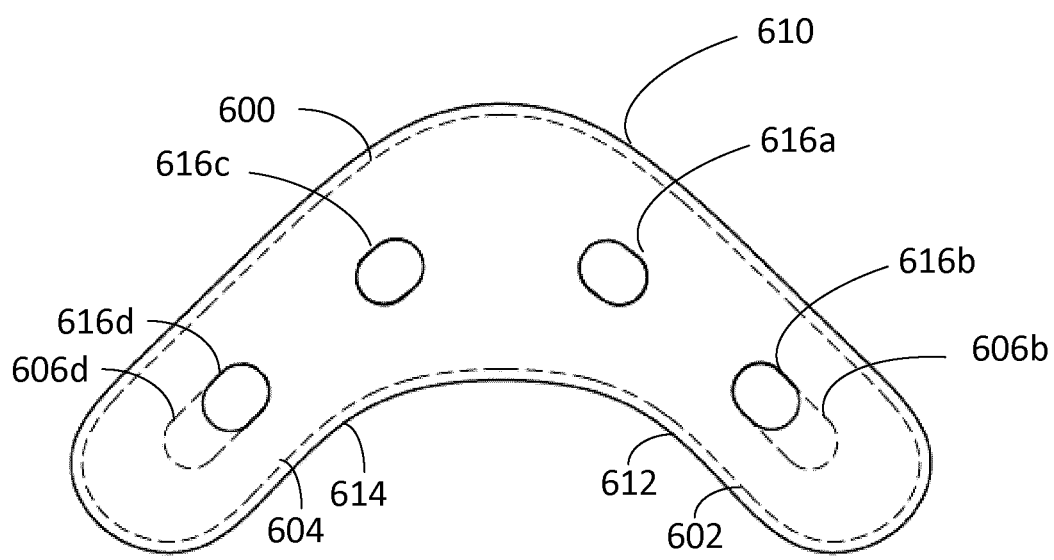
FIG. 6 is an illustration of the device illustrated in FIGS. 1A and B coupled to the removable adhesive illustrated in FIG. 3 in bottom view. The device is represented by dotted lines.

FIG. 6 illustrates a device according to the present disclosure coupled to an adhesive according to the present disclosure in a bottom view. The device (600; dotted lines) has an L-shaped body comprising a first stem (602) and a second stem (604), the first stem (602) comprising two stimulators (not shown; 606b) for stimulating two regions of an individual's neck on one side of the individual's midline, the second stem (604) comprising another two stimulators (not shown; 606d) for stimulating another two regions of the individual's neck on the second side of the individual's midline. The adhesive (610) has an L-shaped shaped body comprising a first adhesive stem (612) and a second adhesive stem (614), the first adhesive stem (612) comprising two hydrogel regions (616a; 616b). When coupled to the device (600), hydrogel region (616a) is in electrical communication with a stimulator (now shown) in its entirety, and hydrogel region (616b) is in electrical communication with a portion of stimulator (606b). The second stem (614) comprises another two hydrogel regions (616c; 616d). When coupled to the device (600), hydrogel region (616c) is in electrical communication with a stimulator (now shown) in its entirety, and hydrogel region (616d) is in electrical communication with a portion of stimulator (606d).

Figure 7:
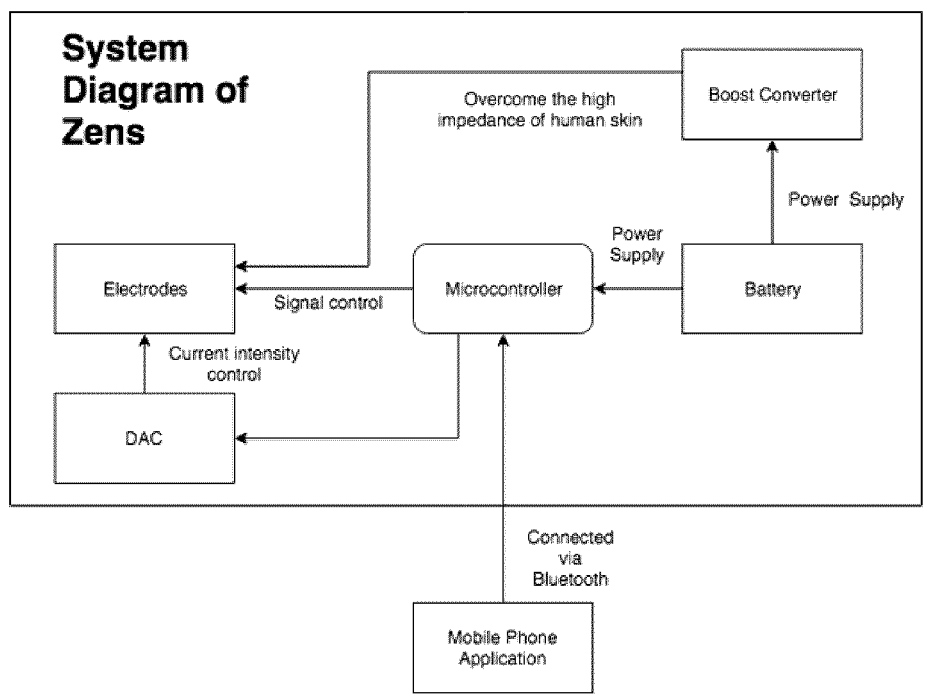
FIG. 7 is a flowchart of an example of the electronics of a device according to the present disclosure.

FIG. 7 is a flowchart of an example of the electronics of a device according to the present disclosure. The device is controlled by a microcontroller which is powered by a Li-ion battery. The device uses a boost converter to supply sufficient voltage to penetrate human skin in order to stimulate the targeted nerve. The boost converter is powered by the same Li-ion battery. The waveform pattern is generated from the microcontroller, which is amplified to the boosted voltage by a multi-channel op-amp. The current supplied to a user is clamped and controlled by a DAC which is further controlled by the same microcontroller. A mobile application is used to send commands to the microcontroller according to the users needs.

Figure 8:
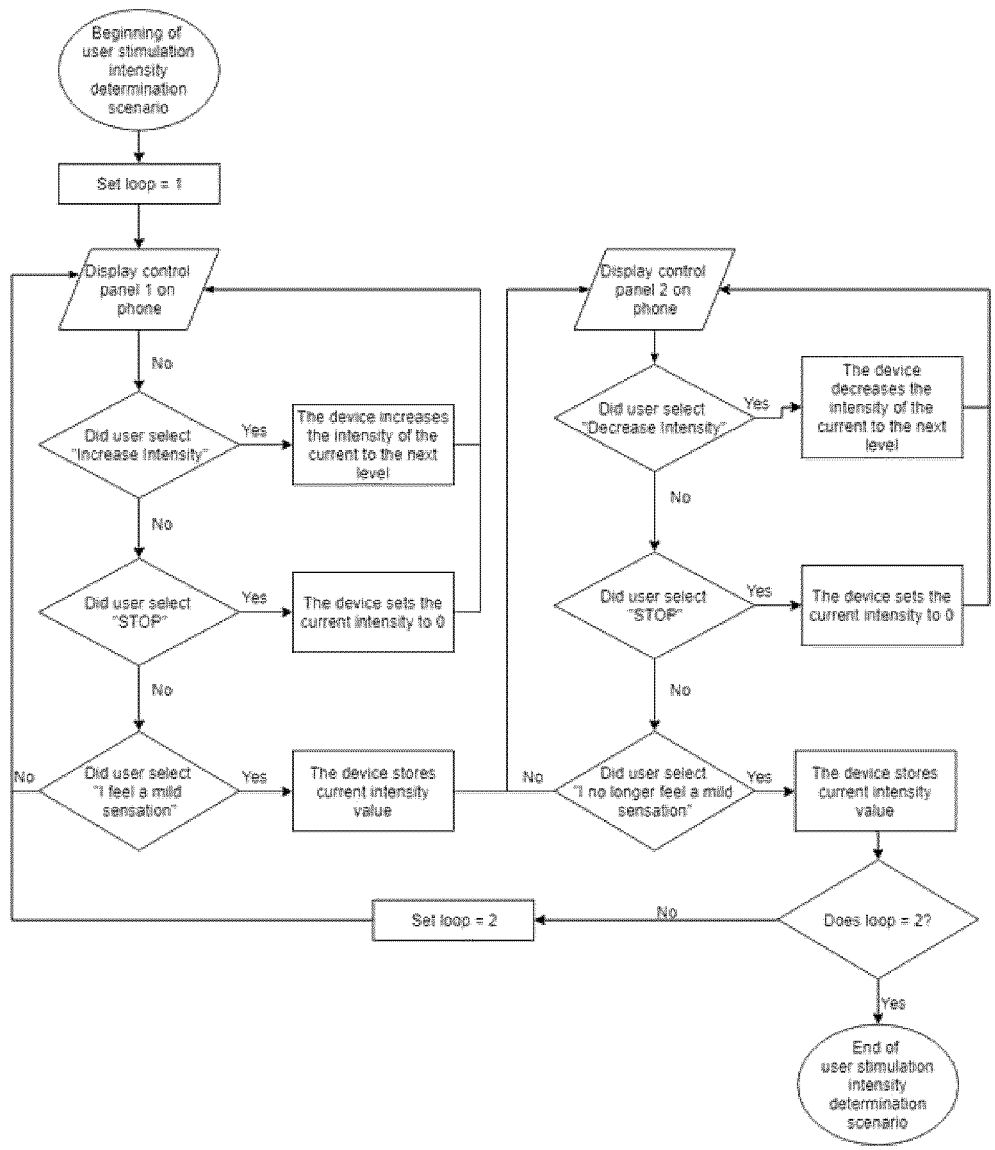
FIG. 8 is a flowchart of an example of a calibration procedure for using a device according to the present disclosure.

FIG. 8 is a flowchart of an example of a calibration procedure for using a device according to the present disclosure. The titration method is used to determine a comfortable intensity of stimulation for a user. During the determination of the stimulation intensity, the user is asked to firstly increase the intensity of the stimulation one step at a time until they have a mild sensation of the stimulation. The user is then asked to decrease the stimulation intensity until they no longer have a mild sensation of the stimulation. This processes is repeated twice so that the mobile application captures two intensity values for the high intensity threshold and two values for the low intensity threshold. The mobile application takes the average of the four values as the setup stimulation intensity.

Figure 9:
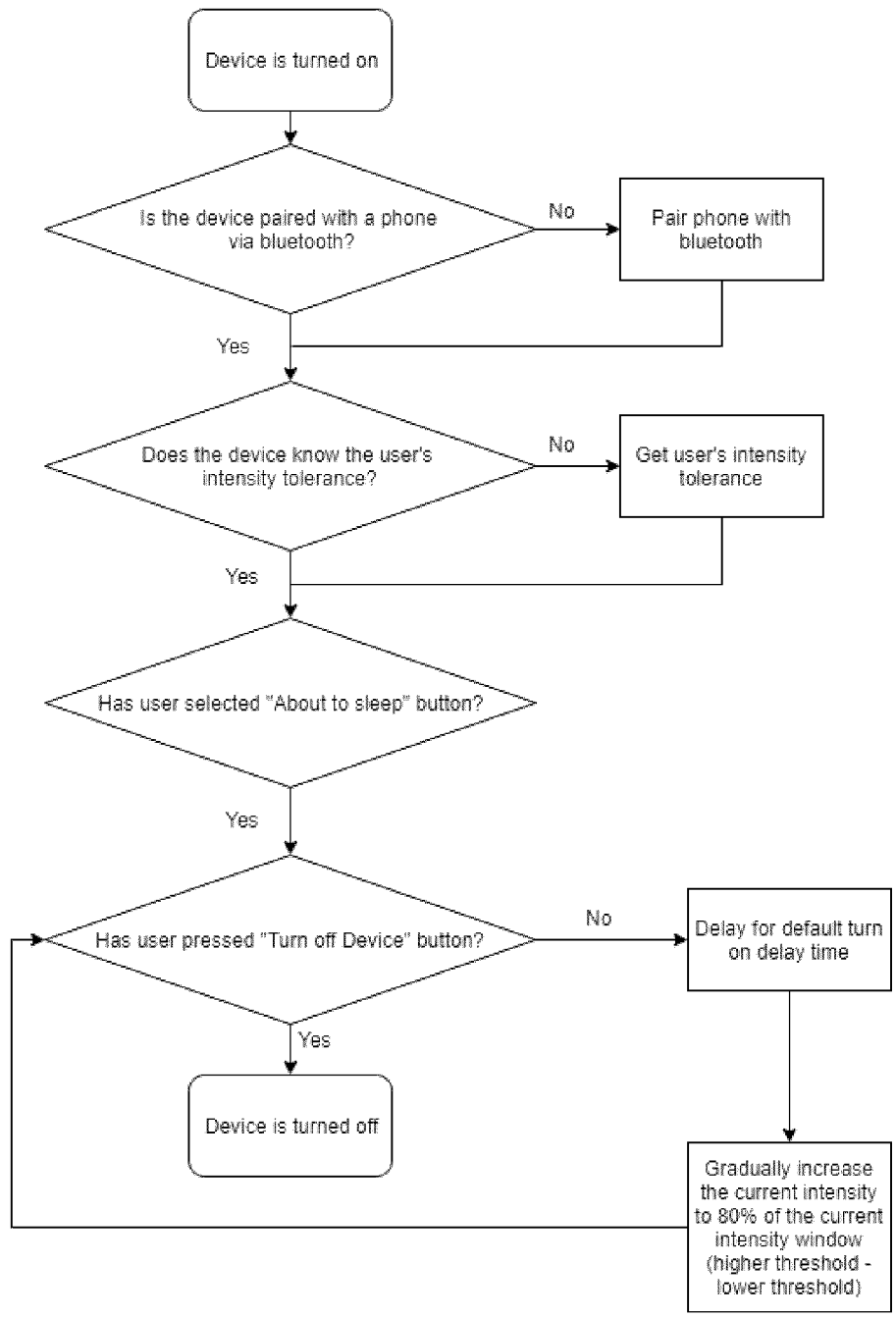
FIG. 9 is a flowchart of an example of a method of using a device according to the present disclosure.

FIG. 9 is a flowchart of an example of a method of using a device according to the present disclosure. The device is tuned on and paired with a user's mobile phone. A mobile application directs the user to either a stimulation intensity determination page or an "About to sleep" page. Once the stimulation intensity is setup, and the user has clicked "About to sleep" button, the stimulation will turn on until the user terminates the stimulation when they wake up.

References to other documents are made throughout this disclosure. Such documents are incorporated herein by reference in their entirety.

EXAMPLES

Example 1

Testing Regions of Stimulation

An experiment was performed to test the regions of a participant's neck for stimulation to decrease snoring. Two electrodes were placed on one side of the individual's midline in the anterior triangle region. The individual's snoring increased after stimulation. Without being bound by theory, the inventors believe that simulating only one side of the individual's midline caused the participant's tongue to move to one side and partially block the participant's airway thereby causes snoring.

Example 2

Testing Regions of Stimulation

Experiments were performed to test the regions of an individual's neck for stimulation to decrease snoring. A pair of electrodes were placed on the individual's neck in the anterior triangle region, one on either side of the individual's midline. The individual's genioglossus muscles were not sufficiently stimulated to decrease the individual's snoring. A similar experiment was performed placing a pair of electrodes on an individual's neck in the anterior triangle region posterior to the above-mentioned placement of electrodes, one on either side of the individual's midline. Similarly, the individual's genioglossus muscles were not sufficiently stimulated to decrease the individual's snoring. Without being bound by theory, the inventors believe that stimulating only one region of each of the hypoglossal nerves was insufficient to stimulate the genioglossus muscles because the electric current was passed across the hypoglossal nerves. The inventors surprisingly found that stimulating at least two regions of each hypoglossal nerve caused the electric current to move down/along the hypoglossal nerve resulting in sufficient genioglossus muscle contraction and a decrease in snoring.

Example 3

Ultrasound Location Test

The first set of experiments tested the hypothesis of which location in the submandibular region when stimulating the hypoglossal nerve can generate the largest muscle contraction or flexing of the tongue muscle. The purpose of this study was to determine the effectiveness of using transcutaneous electrical nerve stimulation-based technology to target the hypoglossal nerve to contract the genioglossus muscle, and therefore open the upper airway to improve breathing abilities of the study participants.

The sample size of this test was ten participants, ranging in age from 24 to 60 years old. All of the participants had a history of chronic snoring for at least four years and one participant had been diagnosed with obstructive sleep apnea. The participants were told to shave any facial hair in advance of the tests. A hand-held ultrasound by Clarius8, was used to examine the upper airway while using the off-the-shelf transcutaneous electrostimulation device altered for the use of the test to stimulate the hypoglossal nerve. The tests using the ultrasound measured on average 5.3 cm depth into the submandibular region to show the back of the tongue. The probe was placed in the sagittal and coronal view between the electrodes on the midline and under the chin. The initial test waveforms were between 30 Hz to 100 Hz with pulse widths of 50 µs to 250 µs.

The following placements were tested: two of the at least four regions of a participant's neck in the anterior triangle regions on opposing sides of the participant's midline. Second, another two of the at least four regions of the participant's neck are anterior triangle regions on opposing sides of the participant's midline, posterior to the two of the at least four regions. Third, stimulating on two of the at least four regions of the participant's neck in the anterior triangle regions on the left side of the participant's midline. Fourth, stimulating on two of the at least four regions of the participant's neck in the anterior triangle regions on the right side of the participant's midline.

The locations tested were selected after mapping out the hypoglossal nerve in relation to the carotid artery, lower mandible and submandibular region. When placing two electrodes on two regions on one side of the midline, the participant found it more difficult to breathe and their tongue did not noticeably contract. When placing two electrodes on one region on both sides of the midline either posterior or anterior the participant's tongue contracted but did not move the tongue evenly to clear the airway. The tongue did not contract reliably as it would contract on one side of the genioglossus muscle or not move at all.

Example 4

Overnight Sleep Test

The second experiment tested the hypothesis of whether the aforementioned hypothesized placement could reduce the volume of snoring given two waveforms. Additionally, this test included determining the snoring baseline of the test subject.

The sample size of this test was four participants, ranging in age from 24 to 60 years old. Four participants were recruited for an overnight sleep test. The test was conducted with an off the shelf transcutaneous electric nerve stimulation device that we were able to alter to meet the needs of our waveform and testing. Some of the participants had obstructive sleep apnea and others where chronic snorers. The participants had to be clean shaven to participate in the test. Participants were asked not to drink or smoke before going to bed. A third party recording program was used to record the volume of snoring and filter out the ambient environmental noise associated with sleeping.

The participants recorded their snoring for 2 to 3 nights before the sleep test to set a base for their snoring levels. The third party recording program documented the peaks and lows of the volume of snoring that could be compared night over night. The participants slept with the device turned on for two nights while their snoring was being recorded.

The waveforms were determined in advance to the test by using the successful placement determined in Example 3. The outcome was that the majority of the participants had the volume of their snoring reduced and remained asleep throughout the night.

Example 5

Third Party Evaluation

The third experiment tested the hypothesis of whether a third party ultrasound professional, otorhinolaryngology physician, and radiologist physician could replicate or confirm either the positive or negative test results.

The tests were conducted on two participants from Example 3 and four participants at the third party medical clinic facility. The participants from Example 3 were both 25 year old males with a history of chronic snoring. The experiment was conducted with a Siemens ultrasound machine with a curved probe placed under the chin between the electrodes in a coronal view to capture the movement of the genioglossus muscle when given stimulation using our waveform and placements.

In this setting, the placements tested where the following: two of the at least four regions of the participant's neck in the anterior triangle regions on opposing sides of the participant's midline. Second, another two of the at least four regions of the participant's neck are anterior triangle regions on opposing sides of the participant's midline, posterior to the two of the at least four regions. Third, stimulating on two of the at least four regions of the participant's neck in the anterior triangle regions on the left side of the participant's midline. Fourth, stimulating on two of the at least four regions of the participant's neck in the anterior triangle regions on the right side of the participant's midline.

The collective physicians confirmed that stimulating the submandibular region on the same side of the midline caused the airway to become blocked by the tongue. These results also determined that either the posterior or anterior submandibular region placement on its own on either side of the midline does not sufficiently stimulate the nerve to clear the airway.

Example 6

Ultrasound Confirmation

This test evaluated the hypothesis of using four electrodes in four submandibular regions to increase oxygen passing through the airway. The purpose of this study was to determine the effectiveness of using transcutaneous electrical nerve stimulation-based technology to target the hypoglossal nerve to contract the genioglossus muscle and the hyoglossus muscle, the styoglossus muscle, the superior longitudinal muscle, the inferior longitudinal muscle, the transverse muscle, the vertical muscle, or a combination thereof. This type of stimulation will open the upper airway to improve the breathing abilities of the study participants.

The sample size of this test was five participants, ranging in age from 24 to 29 years old. All of the participants had a history of chronic snoring for at least two years. Participants were told to shave any facial hair in advance of the tests. A hand-held ultrasound by Clarius8, was used to examine the upper airway while using an off-the-shelf transcutaneous electrical nerve stimulation device altered for the use of the test to stimulate the hypoglossal nerve. The tests using the ultrasound measured, on average, 5.3 cm depth into the submandibular region to show the back of the tongue. The probe was placed in the sagittal and coronal view between the electrodes on the midline and under the chin. The waveforms tested were 2 Hz to 50 Hz and 100 µs to 400 µs.

The locations tested were selected after mapping out the mandibular, submandibular triangle region, and hypoglossal nerve and the genioglossus muscle, the hyoglossus muscle, the styoglossus muscle, the superior longitudinal muscle, the inferior longitudinal muscle, the transverse muscle, the vertical muscle, or a combination thereof. The experiment determined that placing multiple electrodes on either side of the midline produced the largest contraction in the tongue given a mild level of stimulation. The larger contraction signals that the airway was being cleared allowing for more air and/or oxygen to pass through. The overall conclusion being that stimulating the four submandibular regions of a participant's neck, wherein two of the at least four regions of the participant's neck are anterior triangle regions on opposing sides of the participant's midline, and another two of the at least four regions of the participant's neck are anterior triangle regions on opposing sides of the participant's midline, posterior to the two of the at least four regions is most effective at increasing tidal airflow and oxygen levels. The conclusion is reached by the operator of the test being able to monitor tongue contractions when the device is turned on as compared to when the device is turned off. The tongue contractions observed range between 2 mm to 3 mm. The successful locations are recorded and incorporated into the design of the device.

Example 7

Device Placement

The inventors' placement for the herein disclosed device (the "ZENS") is based on secondary anthropometric data and confirmed by conducting primary investigations. ZENS targets four specific locations of stimulation to optimize treatment effectiveness. The placement of these four locations was designed to optimize transcutaneous activation of the distal hypoglossal nerve involving the medial hypoglossal nerve branch. A secondary design objective was to select a placement which also stimulates additional superficial secondary muscle groups with the waveform as it penetrates to the genioglossus (GG). These muscle groups include the oblique genioglossus (GGo) and selected suprahyoid groups which, when activated, would pull the hyoid anteriorly to further increase the patency of the airway.

Figure 10:
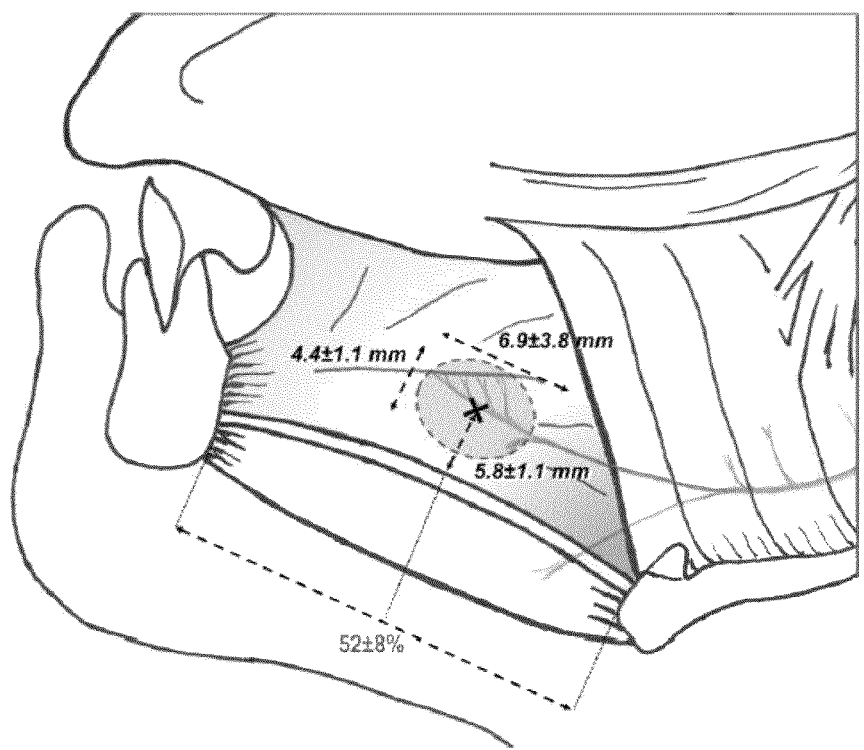
FIG. 10 is an illustration of an example of the placement of a device according to the present disclosure on an individual's neck.

Viewed from the sagittal plane, the horizontal genioglossus (GGh) and GGo branches are located between 52±8% of hyoid bone and mandibular symphysis, and the inferior border of 5.8±1.1 mm. As shown in FIG. 10, the region of stimulation is a 4.4±1.1 by 6.9±3.8 mm. Additional materials supporting shape, size and understanding of various jaw structures are were gathered from the anthropometric data collected by Aleš Hrdlička.

Study Design: Tests were conducted using an ultrasound to monitor tongue contractions while the user was wearing either an off-the-shelf TENS machine altered for the inventors' purpose or a ZENS prototype; transcutaneous hypoglossal nerve stimulation device. The purpose was to design a device that the user can put on simply each time and observe a tongue contraction.

Study Procedure: The subjects underwent initial screening assessments including medical history and ability to follow instructions. The sample size of this test was at least 5 participants between the ages of 18 and 40 years old per design test.

The participants (clean shaven) were asked to lay on their back for the duration of the test. The inventors' positioned the ultrasound in the submandibular region taking a live image from the sagittal view. The inventors recorded video while the participants moved their tongue in a certain pattern. The inventors placed the ZENS device on the user for them and turned on the device. The inventors requested that the participants lay still and breathe slowly and deeply while the ultrasound recorded a video while the device was on.

Equipment: The test was conducted with a ZENS prototype; transcutaneous hypoglossal nerve stimulation device, waveform and testing. This device uses ZENS custom waveform, software, and adhesive. The adhesive is a double-sided daily disposable adhesive that acts as the medium between the device and the skin. The adhesive is designed and manufactured by the inventors. Clarius8 hand help ultrasound was used to record images from the tongue.

Conclusion: The results was the range of potential placements that the ZENS device would operate in and still be effective. The conclusion is reached by the operator of the test being able to monitor tongue contractions when the device is turned on as compared to when the device is turned off. The tongue contractions observed range between 2 mm to 3 mm. The successful locations are recorded and incorporated into the design of the device.

Example 8

Initial Tests to Investigate the Safety and Feasibility of Transcutaneous Stimulation of the Hypoglossal Nerve for the Treatment of Primary Snoring Using the ZENS Transcutaneous Nerve Stimulator The purposes of this test was to determine if the herein disclosed device was able to reduce snoring and or mild obstructive sleep apnea by reducing the duration, frequency, and intensity of chronic snoring to measuring decibel sound levels and other quality of health metrics.

Study Design: Tests were conducted at the participants' homes, open label to evaluate the use of a ZENS transcutaneous hypoglossal nerve stimulator for reducing snoring in primary snorers and symptomatic/non-symptomatic mild obstructive sleep apnea.

Study Procedure: The subjects underwent initial screening assessments including medical history and ability to follow instructions. The sample size of this test was at least 10 participants between the ages of 18 and 60 years old.

The participants were given visual and verbal instructions on how to use the device and record their respiratory effort at night. The participants were asked to record their snoring for at least 2 nights previous to gather an average baseline to compare to their snoring levels when using the device.

Some of the participants had obstructive sleep apnea and others where chronic snorers. The participants had to be clean shaven to participate in the test. Participants were asked not to drink or smoke before going to bed. A 3rd party recording program was used to record the volume of snoring and filter out the ambient environmental noise associated with sleeping.

Equipment: The test was conducted with a ZENS prototype; transcutaneous hypoglossal nerve stimulation device, waveform and testing. This device uses ZENS custom waveform, software, and adhesive. The adhesive is a double-sided daily disposable adhesive that acts as the medium between the device and the skin. The adhesive is designed and manufactured by the inventors. The device is controlled using ZENS mobile application on Xaiomi mobile phones. The Xaiomi mobile phones were also used for all participants to use the 3rd party monitoring respiratory effort app.

Conclusion: The 3rd party recording program documented the peaks and lows of the volume of snoring that could be compared night over night. The different levels of intensity were sorted into quiet, heavy breathing, loud snoring, and epic snoring. An average person who is a chronic snorer or has mild OSA that sleeps for about 8 hours might have about 20 to 30 minutes of epic snoring and about 1 hour 30 minutes to 2 hours loud snoring. When using the presently disclosed device, on average, their epic snoring was minimal and their loud snoring was reduced significantly, with the majority of their night recorded as quiet (no snoring at all) or heavy breathing (note considered snoring, but louder than quiet). This data supported the primary endpoint of reducing the duration, intensity, and frequency of chronic snoring using decibel levels to compare data sets. The inventors observed up to 70% reductions of intensity and duration as measured by the third-party program. Some of the devices used did not have the battery capacity to last all night with the treatment on. It can be noted in the data the approximate time when the device ran out of power, because snoring increased after the battery on the device was zero. Based on the observed results of the compilation of testing data thus far, it can be concluded that there is enough evidence that the ZENS can activate the muscles in the upper airway to externally reduce airway restrictions and/or increase airway patency.

Example 9

Future Test—Efficacy and the Safety/Tolerability of the ZENS Transcutaneous Nerve Stimulator in Primary Snorers and those with Mild Obstructive Sleep Apnea (OSA)

The primary objective of this study is to evaluate the efficacy and the safety/tolerability of the ZENS transcutaneous nerve stimulator in primary snorers and those with mild obstructive sleep apnea (OSA). The hypothesis is to determine if the endpoints of the study are statistically strong enough for both chronic snoring and mild obstructive sleep apnea.

Study Design: Single-center, open label randomized cross-over sleep study of the ZENS transcutaneous hypoglossal nerve stimulator in the "on" (active) versus "off" (passive) setting during a single over-night study. The inclusion criteria for the study are based on the following; aged 18 years or older, willing and able to provide written informed consent, BMI <35 and/or neck circumference <18 inches, history of snoring for the majority of the night, 12 or more of the last 14 nights, etc. The exclusion criteria is based on the following: prior diagnosis of moderate or severe Obstructive Sleep Apnea (OSA), known sleep disturbance other than snoring (i.e., comorbid insomnia), use of sedatives, hypnotics, recreational drug or alcohol in the 24 hours prior to the over-night visit, etc.

Study Procedure: The subjects will undergo initial screening assessments including medical history and ability to follow instructions. The sample size will be approximately 20 to 30 participants.

The user will participate in an overnight level I sleep study in a sleep clinic. The participant will sleep in a semi-private room while being monitored by technicians. The devices will be turned 'on' active and 'off' inactive for half of the night. The user will not know which half of the night the device will be 'on' or 'off' for.

Equipment: The test will be conducted with a ZENS prototype; transcutaneous hypoglossal nerve stimulation device, waveform and testing. This device uses ZENS custom waveform, software, and adhesive. The adhesive will be a double-sided daily disposable adhesive that acts as the medium between the device and the skin. The adhesive is designed and manufactured by the inventors. The device is controlled using ZENS mobile application on Xaiomi mobile phones. The Xaiomi mobile phones will also be used for all participants to use the 3rd party monitoring respiratory effort app. In addition, the user will be connected to a level I sleep study and have a medical grade sound meter positioned to record their snoring (duration, frequency, and intensity).

Conclusion: The results of this study will give evidence to the efficacy of the device.

Example 10

Future Test—Waveform Correctness

The correctness of the waveform is important to the efficacy of treatment. It will increase the chance of successfully stimulating the hypoglossal nerve to contract the genioglossus muscle to help with the closed airway.

Study Design: The waveform correctness test will be conducted in an electronics laboratory. Open label to evaluate the correctness of the inventor's technology, ZENS transcutaneous nerve stimulator's ZENS custom waveform and the tolerance of between the designed ZENS custom waveform and the actual ZENS custom waveform.

Study Procedure: To set up the test, an oscilloscope will be used to record the output waveform. The GND clip of the probe will be hocked onto one of the electrodes from one electrode pair. The probe will be set to hock onto the other electrode from the same electrode pair. The oscilloscope will be set to record the waveform at a rate of 40 kHz. The time interval of the oscilloscope will be set to be 50 us and the voltage will be set to 10V with the probe being set to 10X. A load resistor of 1.2 KOhms will be connected across the electrodes to imitate the skin impedance of our users.

After the set-up, the ZENS prototype will be set into THERAPY_ON mode and read the ZENS custom output waveform from the oscilloscope. The test passes if the shape of the ZENS custom output waveform showing on the oscilloscope is the same as the designed ZENS custom output waveform shape with pre-defined tolerance.

Equipment: An oscilloscope and the ZENS prototype from Zennea Technologies.

Conclusion: The data acquired from the test will validate the hypothesis of using the ZENS custom waveform is effective to reducing OSA events.

Example 11

Future Test—Adhesive Effectiveness

Adhesive effectiveness has several important criteria for using the raw materials prior to making or testing the adhesives. ISO 10993 (sensitization, cytotoxicity, and Irritation) certifications should be verified, ability of raw material to maintain its conductivity abilities, and ability to maintain its tact while not damaging the skin. The ability for the adhesive to meet the above objective criteria prior to being tested for subjective criteria limits the different hydrogels and pressure dressings that can be selected for ZENS device use. ZENS adhesive testing will be conducted on a variety of individuals to ensure it can pass the material feature requirements on different skin types. The purpose of these tests is to test skin sensitivity on a variety of people for subjective purposes after the adhesives pass the objective manufacturing criteria.

Study Design: Tests will be completed in an uncontrolled environment (participant's homes, offices, public places). Open label to evaluate the use of the inventors' Technologies, ZENS adhesive's raw materials to maintain tact, act as medium to deliver stimulation and do so without harming the skin.

Study Procedure: ZENS adhesive patch testing will be conducted as per dermatologist Canada standards.

The only exclusion criteria of participants being the skin on the upper back of participants cannot be abnormal or damaged.

To set up the test, the administrator of the test will prepare the pressure dressing or hydrogel raw material samples onto a 3M Tegaderm patch in a 3 by 2 shape. The administrator will clean the participant's back with an alcohol-based wipe. The patch of raw material adhesives will be placed onto the back of the participants for 12 consecutive hours. When the patch is removed the before and after images will be compared.

If the adhesive raw materials pass this test then they are made into ZENS adhesives. The full adhesives (pressure dressing and hydrogel in the shape of ZENS device) will then tested for tact and comfort. The adhesives will be given to participants with a ZENS device to wear overnight. The hypothesis being, will the device remain on the participants' submandibular region overnight? The administrator of the test will clean the participants' submandibular region, and apply the adhesive to the device and the device to the submandibular region. Before and after pictures will be taken. If the device falls off during the night the test will be a fail. If the device stays on overnight the test will be a success.

Equipment: ZENS adhesive material candidates will be precut in a sterile environment using a di-cutter. Hydrogel or hypo allogenic pressure dressings will be used in these tests. ZENS devices will not be active during this test.

Conclusion: The data analyzed from these tests will be reviewed for skin marking or damage and device functionality. From these tests, the inventors' will be able to determine what is the range of successful adhesive materials that can successfully deliver the stimulation and remain on the users face.

In the preceding description, for purposes of explanation, numerous details are set forth in order to provide a thorough understanding of the examples. However, it will be apparent to one skilled in the art that these specific details are not required. The above-described examples are intended to be examples only. Alterations, modifications and variations can be effected to the particular examples by those of skill in the art. The scope of the claims should not be limited by the particular examples set forth herein, but should be construed in a manner consistent with the specification as a whole.

What is claimed is:

1. A device for decreasing snoring, obstructive sleep apnea, upper airway resistance condition, or a combination thereof in an individual, the device comprising:
    four transcutaneous stimulators couplable to the individual's neck and/or chin using a removable adhesive, each transcutaneous stimulator being configured to stimulate a region of the individual's neck,
        wherein two of the four transcutaneous stimulators are configured to stimulate first and second regions of the individual's neck that are anterior triangle regions on opposing sides of the individual's midline, where a hypoglossal nerve splits between a medial contingent and a lateral contingent, and
        wherein two of the four transcutaneous stimulators are configured to stimulate third and fourth regions of the individual's neck that are anterior triangle regions on opposing sides of individual's midline, said third and fourth regions of the individual's neck being posterior to the first and second regions of the individual's neck; and
    a processor in electrical communication with the four transcutaneous stimulators, said processor being configured to control the transcutaneous stimulation,
        wherein the device has an L-shaped body comprising a first stem and a second stem, the first stem comprising two of the four transcutaneous stimulators configured to stimulate the first and second regions of the individual's neck on a first side of the individual's midline, the second stem comprising two of the four transcutaneous stimulators configured to stimulate the third and fourth regions of the individual's neck on a second side of the individual's midline.

2. The device according to claim 1, wherein the device is configured to deliver at least two bi-phasic waveform modulations, wherein at least a first type of the at least two types of biphasic waveform modulations is a low-intensity, high frequency waveform and another type of the at least two types of waveform modulations is a high-intensity, low-frequency waveform.

3. The device according to claim 2, wherein the high-intensity, low-frequency waveform comprises at least two pulses, wherein one pulse of the at least two pulses is positive in magnitude and wherein another pulse of the at least two pulses is negative in magnitude.

4. The device according to claim 1, wherein the processor is configured to incrementally increase/decrease stimulation intensity until a threshold is met.

5. The device according to claim 1, wherein the processor is configured to adjust stimulation intensity in response to a vital sign collected from the individual while the individual is asleep.

6. The device according to claim 1, wherein the four transcutaneous stimulators are gold-plated or silver-plated copper electrodes.

7. The device according to claim 1, wherein the four transcutaneous stimulators are oriented in fixed positions relative to one another for stimulating the four regions of the individual's neck.

8. The device according to claim 1,
wherein the device is configured to be couplable to an adhesive component that is in electrical communication with at least a portion of each of the four transcutaneous stimulators, and
wherein the orientation of the adhesive component, when coupled to the device, conducts the electrical stimulation from the four transcutaneous stimulators to the first, second, third, and fourth regions of the individual's neck and prevents conduction of the electrical stimulation from the four transcutaneous stimulators to the individual's neck at regions other than the first, second, third, and fourth regions.

9. The device according to claim 8, further comprising the adhesive component, wherein the adhesive component comprises conductive and nonconductive regions, said conductive regions being configured to facilitate electrical communication between each of the four transcutaneous stimulators and the respective regions on the individual's neck.

10. The device according to claim 9, wherein said nonconductive regions of the adhesive component are configured to prevent electrical stimulation from being conducted outside of the four regions of the individual's neck.

11. The device according to claim 9, wherein each of the conductive regions are composed of a hydrogel.

12. A system for decreasing snoring, obstructive sleep apnea, or a combination thereof in an individual, the system comprising:
the device of claim 1;
a power source coupled to the device for providing an electrical signal to the four transcutaneous stimulators; and a user interface in wireless communication with the device of claim 1.

13. The system of claim 12, further comprising a sleep sensor in wireless communication with the device of claim 1.

14. A method for decreasing snoring, obstructive sleep apnea, or a combination thereof in an individual, the method comprising:
applying transcutaneous stimulation to four regions of the individual's neck, said regions comprising a first anterior triangle region and a second anterior triangle region on opposing sides of the individual's midline; and a third anterior triangle region and a fourth anterior triangle region on opposing sides of the individual's midline, said third and fourth anterior triangle regions being located posterior to the first anterior triangle region and the second anterior triangle region, respectively.

15. The method of claim 14, wherein the transcutaneous stimulation comprises:
passing current from the first anterior triangle region to the third anterior triangle region; and
passing current from the second anterior triangle region to the fourth anterior triangle region.

16. The method of claim 14, wherein the transcutaneous stimulation is a current produced by two types of waveform modulations.

17. The method of claim 16, wherein the two types of waveform modulations are a low-intensity, high-frequency waveform and a high-intensity, low-frequency waveform.

18. The method of claim 17, wherein the high-intensity, low-frequency waveform comprises at least a first pulse and a second pulse, the first pulse being positive in magnitude and the second pulse being negative in magnitude.

19. The method of claim 17, wherein the low-intensity, high-frequency waveform comprises at least a first pulse and a second pulse, the first pulse being positive in magnitude and the second pulse being negative in magnitude.

* * * * *